US006284219B1

(12) United States Patent
Ajami

(10) Patent No.: US 6,284,219 B1
(45) Date of Patent: *Sep. 4, 2001

(54) IN VIVO DETERMINATION OF METABOLIC FUNCTION FOR USE IN THERAPY MANAGEMENT

(75) Inventor: Alfred M. Ajami, Brookline, MA (US)

(73) Assignee: Phenome Sciences Inc., Woburn, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/107,965

(22) Filed: Jun. 30, 1998

(51) Int. Cl.[7] ............................ A61K 51/00; A61M 36/14

(52) U.S. Cl. ............................ 424/1.11; 424/1.81; 435/4

(58) Field of Search .................................. 424/1.11, 1.53, 424/1.65, 1.81, 9.2; 435/4, 183, 188, 814; 250/472.1; 600/9

(56) References Cited

U.S. PATENT DOCUMENTS

| | | | |
|---|---|---|---|
| 4,298,347 | 11/1981 | Walsh | 23/230 B |
| 4,665,082 | 5/1987 | Meister et al. | 514/365 |
| 4,676,974 | 6/1987 | Hofmann et al. | 424/9 |
| 4,830,010 | 5/1989 | Marshall | 128/630 |
| 4,940,658 | 7/1990 | Allen et al. | 435/4 |
| 4,947,861 | 8/1990 | Hamilton | 128/719 |
| 5,100,779 | 3/1992 | Watkins | 435/25 |
| 5,212,096 | 5/1993 | Kolhouse et al. | 436/93 |
| 5,233,997 | 8/1993 | Klein et al. | 128/718 |
| 5,374,560 | 12/1994 | Allen et al. | 436/129 |
| 5,386,832 | 2/1995 | Wagner et al. | 128/665 |
| 5,413,917 | 5/1995 | Malloy et al. | 435/35 |
| 5,432,058 | 7/1995 | Lange, III et al. | 435/11 |
| 5,438,017 | 8/1995 | Allen et al. | 436/89 |
| 5,439,803 | 8/1995 | Ross et al. | 435/14 |
| 5,449,688 | 9/1995 | Wahl et al. | 514/546 |
| 5,466,434 | 11/1995 | Kyle | 424/9 |
| 5,506,147 | 4/1996 | Kolhouse et al. | 436/86 |
| 5,597,548 | 1/1997 | Sherry et al. | 424/9.3 |
| 5,628,328 | 5/1997 | Nissen et al. | 128/774 |
| 5,707,602 | 1/1998 | Klein | 424/1.17 |
| 5,756,067 | 5/1998 | Redgrave et al. | 424/1.81 |
| 5,783,445 | 7/1998 | Murnick | 436/35 |

FOREIGN PATENT DOCUMENTS

| | | |
|---|---|---|
| 26 26 533 | 12/1977 | (DE) . |
| 0253927 | 5/1986 | (EP) ........................ 33/497 |
| 0826377 | 8/1997 | (EP) ............................ A61K/49/00 |
| 825 260 | 2/1998 | (EP) . |
| 826 377 | 3/1998 | (EP) . |
| 966 975 | 12/1999 | (EP) . |
| 93/05780 | 4/1993 | (WO) . |
| WO96/14091 | 5/1995 | (WO) . |
| WO97/35622 | 10/1997 | (WO) . |
| WO98/24362 | 6/1998 | (WO) . |
| WO98/29728 | 7/1998 | (WO) . |

OTHER PUBLICATIONS

Dox et al, 1993, The Harper Collins Illustrated Medical Dictionary, pp. 63, 260, & 377.*

Adler et al., "New Methods for Assessment of Enzyme Activity: Do They Help to Optimize Enzyme Treatment?" *Digestion* 54:3–9 (1993).

Arnaud et al., "Study of the Demethylation of [1,3, 7–Me–$^{13}$C] Caffeine in Man Using Respiratory Exchange Measurements," *Biomed. Mass. Spec.* 7:521–524 (1980).

Arnold et al., "Increased Whole Body Protein Breakdown Predominates over Increased Whole Body Protein Synthesis in Multiple Organ Failure," *Clinical Science* 84:655–661 (1993).

Baker et al., "The Aminopyrine Breath Test Does Not Correlate with Histologic Disease Severity in Patients with Cholestasis," *Hepatology* 7:464–467 (1987).

Barr et al., "Isotope Dilution–Mass Spectrometric Quantification of Specific Proteins: Model Application with Apolipoprotein A–1," *Clinical Chemistry* 42:1676–1682 (1996).

Barshop et al., "Metabolism of 1–$^{13}$C–Propionate In Vitro in Patients with Disorders of Propionate Metabolism," *Pediatric Research* 30:15–22 (1991).

Barstow et al., "Influence of Increased Metabolic Rate on [$^{13}$C]bicarbonate Washout Kinetics," *American Physiological Society* 0363:R163–R171 (1990).

(List continued on next page.)

Primary Examiner—José G. Dees
Assistant Examiner—Dameron L. Jones
(74) Attorney, Agent, or Firm—Weingarten, Schurgin, Gagnebin & Hayes LLP

(57) ABSTRACT

It is an object of the present invention to provide in vivo analytical methods that allow for diagnosis and management of therapy for diseases involving discrete biochemical pathways. In the method of the invention, a labelled tracer probe, a specifically designed substrate of a "gateway" enzyme, an enzyme marking a regulatory point in a discrete biochemical pathway, is administered to a subject; a labelled product of the action of the enzyme is measured; and the appearance and concentration of the product are related to the disease condition of interest. Determination of the rate of substrate-product conversion of the gateway enzyme allows for the analysis to be made. The method involves administering a defined amount of a labelled "metaprobe" substrate of the gateway enzyme to a subject, at a site that provides access to a desired pool of the gateway enzyme in the subject, and measuring the amount of the chosen labelled product. The presence and amount of the chosen labelled product in, e.g., the breath, definitively indicates that the labelled metaprobe has been metabolized by the specific enzyme in the specific biochemical pathway under consideration, and from the calculated rate of substrate-product conversion by the gateway enzyme, the desired diagnostic determination may be made.

31 Claims, 15 Drawing Sheets-

OTHER PUBLICATIONS

Beaufort–Krol et al., "Determination of Organ Substrate Oxidation In Vivo by Measurement of $^{13}CO_2$ Concentration in Blood." *J. Mass. Spec.* 33:328–333 (1998).

Beaufrere et al., "Whole Body Protein Turnover Measured with $^{13}C$–Leucine and Energy Expenditure in Preterm Infants," *Pediatric Research* 28:147–152 (1990).

Beaumier et al., "Urea Cycle Intermediate Kinetics and Nitrate Excretion at Normal and "Therapeutic" Intakes of Arginine in Humans," *American Physiological Society* 0193:E884–E896 (1995).

Bielanski et al., "New Approach to $^{13}C$–Urea Breath Test: Capsule–Based Modification with Low–Dose of $^{13}C$–Urea in the Diagnosis of *Helicobacter Pylori* Infection," *J. Physiol and Pharm* 47:545–553 (1996).

Bircher et al., "Exhalation of Isotopic $CO_2$," *Methods in Enzymology* 77:3–9 (1981).

Bjorkmann et al., "$^{13}C$–Bicarbonate Breath Test as a Measure of Gastric Emptying," *American J. Gastro.* 86:821–823 (1991).

Blanchette et al., "Determination of Hydrogen Sulfide and Methyl Mercaptan in Mouth Air at the Parts–per–Billion Level by Gas Chromatography," *Analytical Chemistry* 48:729–731 (1976).

Bode et al., "Variation in the $^{13}C$–Urea Breath Test Value by Nationality in *Helicobacter pylori*–Infected Children," *Scandinavian Journal of Gastroenterology* 33:468–472 (1998).

Branden et al., The [$^{13}C$]Acetate Breath Test Accurately Reflects Gastric Emptying of Liquids in Both Liquid and Semisolid Test Meals, *Gastroenterology* 108:1048–1055 (1995).

Branden et al., "More Convenient $^{13}C$–Urea Breath Test Modifications Still Meet the Criteria for Valid Diagnosis of *Helicobacter pylori* Infection," *Z Gastrodeutrol* 32:198–202 (1994).

Brenna J.T., "Use of Stable Isotopes to Study Fatty Acid and Lipoprotein Metabolism in Man," *Prostaglandins. Leukotrienes and Essential Fatty Acids* 57:467–472 (1997).

Broesicke et al., "The $^{13}C$–Carbon Dioxide Breath Test for Diagnosis of Inheritable Metabolic Disease," *Nippon Jyo Masu Superkotoro* 17:39–44 (1992).

Brossard et al., "Stable Isotope Tracer and Gas–Chromatography Combustion Isotope Ratio Mass Spectrometry to Study the In Vivo Compartmental Metabolism of Docosahexaenoic Acid," *Analytical Bio.* 220:192–199 (1994).

Burke et al., "L–[1–$^{13}C$]Phenylalanine Oxidation as a Measure of Hepatocyte Functional Capacity in End–Stage Liver Disease," *American J. Surgery* 173:270–274 (1997).

Caprio et al., "Effects of Puberty and Diabetes on Metabolism of Insulin–Sensitive Fuels," *American Physiol. Society* 0193:E885–E891 (1994).

Castillo et al., "Whole Body Nitric Oxide Synthesis in Healthy Men Determined from [$^{15}N$]arginine–to–[$^{15}N$]citrulline Labeling," *Proc. Natl. Acad. Sci.* 93:11460–11465 (1996).

Chen et al., "Mercaptans and Dimethyl Sulfide in the Breath of Patients with Cirrhosis of the Liver," *J. Lab. Clin. Med.* 75:628–635 (1970).

Choi et al., "[$^{13}C$]Octanoic Acid Breath Test for Gastric Emptying of Solids: Accuracy, Reproducibility, and Comparison with Scintigraphy," *Gastroenterology* 112:1155–1162 (1997).

Cimmino et al., "Demonstration of in vivo Metabolic Effects of 3,5–di–iodothyrnine," *J. Endocrinology* 149:319–325 (1996).

Cole et al., "Cholesteryl Octanoate Breath Test," *Gastroenterology* 93:1372–80 (1987).

Cunnane et al., "Utilization of Uniformity Labeled $^{13}C$–Polyunsaturated Fatty Acids in the Synthesis of Long–Cahin Fatty Acids and Chlosterol Accumulating in the Neonatal Rat Brain," *J. Neurochemistry* 62:2429–2436 (1994).

Davidson et al., "Instantaneous and Continuous Measurement of $^{14}C$–Labeled Substrate Oxidation to $^{14}CO_2$ by Minute Tissue Specimens: An Ionization Chamber Method," *Metabolism* 30:596–600 (1981).

Demant et al., "Studies of Alolipoprotein B–100 Metabolism Using Radiotracers and Stable Isotopes," *Eur. J. Peadiatr.* 156:S75–S77 (1997).

Demmelmair et al., "New Insights into Lipid and Fatty Acid Metabolism via Stable Isotopes," *Eur. J. Pediatr.* 156:S70–S74 (1997).

Dorlochter et al., "The [$^{13}C$]methacetin Breath Test: An Alternative for Monitoring Valproic Acid Therapy in Epilepsy During Childhood," *Z Ernahrungswiss* 36:373 (1997).

Eggers et al., "A Methodological Analysis of the $^{13}C$–Urea Breath Test for Detection of *Helicobacter pylori* Infections:" *Eur. J. Gastro. & Hepta.* 2:437–444 (1990).

El–Khoury et al., "Validation of the Tracer–Balance Concept with Reference to Leucine: 24–H Intravenous Tracer Studies with L–[1–$^{13}C$]leucine and [$^{15}N$–$^{15}N$]Urea$^{1-3}$," *Am. J. Clin. Nutr.* 59:1000–11 (1994).

Elsas et al., "Practical Methods to Estimate Whole Body Leucine Oxidation in Maple Syrup Urine Disease," *Peadratic Research* 33:445–451 (1993).

Frenais et al., "High Density Lipoprotein Apolipoprotein AI Kinetics In NIDDM: A Stable Isotope Study," *Diabetologia* 40:578–583 (1997).

Fukagawa et al., "Plasma Methionine and Cysteine Kinetics in Response to an Intravenous Glutathione Infusion in Adult Humans," *American Physiological Society* 0193:E209–E214 (1996).

Ghoos et al., "Measurement of Gastric Emptying Rate of Solids by Means of a Carbon–Labeled Octanoic Breath Test," *Gastroenterology* 104:1640–1647 (1993).

Griffith et al., "Formation of Respiratory $^{14}CO_2$ from Radiolableled Substrates," *Methods in Enzymology* 113:461–468 (1985).

Guo et al., "Free Fatty Acid Turnover Measured Using Ultralow Doses of [U–$^{13}C$]palmitate," *J. Lipid Research* 38:1888–1895 (1997).

Hale et al., "Fatty Acid Oxidation Disorders: A New Class of Metabolic Diseases," *J. Peadiatr.* 121:1–98 (1992).

Halliday et al., "The Degree of Conversion of α–Keto Acids to Valine and Phenylalanine in Health and Uraemia," *Quart. J. Med.* 197:53–62 (1981).

Halliday et al., "Metabolism of $^{13}C$–α–Ketoisovalerate and $^{13}C$–Phenylpyruvate in Man," *Clinical Applications: Protein Metabolism* (1979).

Heine et al., "A Novel Stable Isotope Breath Test: $^{13}C$–Labeled Glycosyl Ureides Used as Noninvasive Markers of Intestinal Transit Time," *American J. Gastro.* 90:93–98 (1995).

Hepner et al., "Breath Tests In Gastroenterology," *Adv. Med.* 23:25–45 (1978).

Herrmann et al., "Dependence of the Utilization of a Phenylalanine–free Amino Acid Mixture on Different Amounts of Single Dose Ingested: A Case Report," *Eur. J. Peadiatr* 153:501–503 (1994).

Hiele et al., "Starch Digestion in Normal Subjects and Patients With Pancreatic Disease, Using a $^{13}CO_2$ Breath Test," *Gastroenterology* 96:503–9 (1989).

Hiroshi et al., "Clinical Application of Breath Analysis for Dimethyl Sulfide Following Ingestion of DL–Methionine" *Clinica Chemica* 93:377–380 (1979).

Hoekstra et al., "Evaluation of $^{13}CO_2$ Breath Tests for the Detection of Fructose Malabsorption," *J. Lab. Clin. Med.* 127:303–309 (1996).

Honkoop et al., "Effect of Lamivudine on Morphology and Function of Mitrochondria in Patients with Chronic Hepatitis B," *Hepatology* 26:211–215 (1997).

Hsu et al., "Metabolism In Vivo of 5–Oxo–L–proline and Its Inhibition by Analogs of 5–Oxo–L–proline," *Methods in Enzymology* 113:468–471 (1995).

Iikura et al., "Study of Liver Function in Infants with Atopic Dermatitis Using the $^{13}C$–Methacetin Breath Test," *Int. Arch. Allergy Immunol.* 107:189–193 (1995).

Iinuma et al., "Utility of the $^{13}C$–Phenacetine Breath Test in Determining Liver Function in Patients with Acute and Chronic Hepatitis," *J. Med. Soc. Toho Univ.* 19:211–222 (1997).

Imura et al., "Utilization of Protein Synthesis of 2–ketoisocaproate Relative to Utilization of Leucine, as Estimated from Exhalation of Labelled $CO_2$," *Clinical Science* 75:301–307 (1998).

Iinuma et al., "$^{13}C$–Phenacetin Breath Test as a Measure of Liver Function in Cirrhotics," *J. Med. Soc. Toho Japan* 44:211–222 (1997).

Irving et al., "The Aminopyrine Breath Test as a Measure of Liver Function," *J. Lab. Clin. Med.* 100:356–373 (1982).

Irving et al., "[$^{13}C$]bicarbonate Kinetics in Humans: Intra– vs. Interindividual Variations," *Amer. J. Physiol* 245:R190–R202 (1983).

Jager–Roman et al., "Development of N–Demethlyase Activity Measured with the $^{13}C$–Aminopyrine Breath Test," *Eur. J. Pediatr* 139:129–134 (1982).

Jakobs et al., "In Vivo Stable Isotope Studies in Three Patients Affected with Mitochondrial Fatty Acid Oxidation Disorders: Limited Diagnostic Use of $1-^{13}$ Fatty Acid Breath Test Using Bolus Technique," *Eur. J. Pediatr* 156:S78–S82 (1997).

Jeukendrup et al., "Metabolic Availability of Medium–Chain Triglycerides Coingested with Carbohydrate during Prolonged Exercise," *American Physiol. Soc.* 0161–756–762 (1995).

Jones et al., "The Effect of Age and Gender on the Metabolic Disposal of [$1-^{13}$]palmitic Acid," *Eur. J. Clin. Nutr.* 52:22–28 (1998).

Kajiwara et al., "Studies on $^{13}C$–Phenacetin Metabolism II: A Combination of Breath Test and Urine Test of In Vivo Metabloites in the Diagnosis of Liver Disease," *Chem. Pharm. Bull* 44:1258–1260 (1996).

Kajiwara et al., "Validity of the $^{13}C$–Urea Breath Test for the Diagnosis of *Helicobacter pylori* Infection," *Chem. Pharm. Bull.* 45:741–743 (1997).

Kalhan et al., "Measurement of Glucose Turnover in the Human Newborn with Glucose–1–13C," *J. Clin. Endocrinol. Metabol.* 43:704–707 (1976).

Kalhan et al., "Estimation of Glucose Turnover with Stable Tracer Glucose–1–$^{13}C$," *J. Lab. Clin. Med.* 89:285–294 (1997).

Kalivianakis et al., "The $^{13}C$–mixed Triglyceride Breath Test in Healthy Adults: Determinants of the $^{13}CO_2$ Response," *Eur. J. Clin. Invest.* 27:434–442 (1997).

Kasho et al., "Feasibility of Analyzing [$^{13}C$]urea Breath Test for *Helicobacter pylori* by Gas Chromatography–Mass Spectrometry in the Selected Ion Monitoring Mode," *Aliment Pharmacol. Ther.* 10:985–995 (1996).

Kato et al., "$^{13}C$–Labeled Trictanoin Breath Test for Exocrine Pancreatic Function Test in Patients after Pancreatoduodenectomy," *America J. Gasrtoent.* 88:64–69 (1993).

Kim et al., "Serum $^{13}C$–Bicarbonate Assay for the Diagnosis of Gastric *Helicobacter pylori* Infection and Response to Treatment," *Gastroenterology* 113:31–37 (1997).

Klatt et al., "Evaluation of the $^{13}C$–methacetin Breath Test for Quantitative Liver Function Testing," *Z Gastroenterol* 35:600–611 (1997).

Klein et al., "Noninvasive Detection of *Helicobacter pylori* Infection in Clinical Practice: The $^{13}C$ Urea Breath Test," *American J. Gastroent.* 91:690–694 (1996).

Kneepkens et al., "Assessment of Oxidative Stress and Antioxidant Status in Humans: The Hydrocarbon Breath Test," *Antioxidant Methodology* 23–38 (1997).

Kohlmuller et al., "Is n–Pentane Really an Index of Lipid Peroxidation in Humans and Animals? A Methodological Reevaluation," *Analytical Biochemistry* 210:268–276 (1993).

Konturek et al., "Disturbed Gastric Motor Activity in Patients with Human Immunodeficiency Virus Infection," *Scand. J. Gastroenterol.* 32:221–225 (1997).

Koletzko et al., "Safety of Stable Isotope Use," *Eur. J. Pediatr* 156:S12–S17 (1997).

Krumbiegel et al., "[$^{15}N$]Methacetin Urine Test to Measure Liver Function: Methodology for Application in Pediatrics," *J. Ped. Gastroent. and Nutr.* 7:333–340 (1988).

Krumbiegel et al., "Nuclear Medicine Liver–Function Tests for Pregnant Women and Children," *Eur. J. Nucl. Med.* 11:58–61 (1985).

Krumbiegel et al., "Nuclear Medicine Liver Function Tests for Pregnant Women and Children: Breath Tests with $^{14}C$–methacetin and $^{13}C$–methacetin," *Eur. J. Nucl. Med.* 10:129–133 (1985).

Kundu et al., "Breath Acetone Analyzer: Diagnostic Tool to Monitor Dietary Fat Loss," *Clin. Chem.* 39:87–92 (1993).

Lane et al., "Drug Pharmacokinetics and the Carbon Dioxide Breath Test," *J. Pharmkin. and Biopharm.* 14:29–49 (1986).

Larsen et al., "Determination of the Exocrine Pancreatic Function with the NBT–PABA Test Using a Novel Dual Isotope Technique and Gas Chromatrography–Mass Spectrometry," *Scand. J. Lab. Invest* 57:159–166 (1997).

Lauterburg et al., "Mitochondrial Dysfunction in Alcoholic Patients as Assessed by Breath Analysis," *Heptaology* 17:418–422 (1993).

Lauterburg et al., "Noninvasive Assessment of Mitochondrial Function by Breath Analysis Using Ketoioscaproic Acid," *Methods in Toxicology* 2:102–106 (1993).

Lauterburg et al., "Noninvasive Assessment of the Effect of Xeonobiotics on Mitochondrial Function in Human Beings: Studies with Acetylsalicylic Acid and Ethanol with the Use of the Carbon $^{13}$–Labeled Ketoisocaproate Breath Test," *J. Lab. Clin. Med.* 125:378–383 (1995).

Leese et al., "Post-exercise Gastric Emptying of Carbohydrate Solutions Determined Using the $^{13}$C Acetate Breath Test," Eur. J. Appl. Physiol. 71:306–310 (1995).

Lemoyne et al., "Breath Pentane Analysis as an Index of Lipid Peroxidation: A Functional Test of Vitamin E Status," Am. J. Clin. Nutr. 46:267–72 (1987).

Lertratanangkoon et al., "Methyl–Donor Deficiency Due to Chemically Induced Glutathione Depletion," Cancer Research 56:995–1005 (1996).

Levy et al., "In Vivo Assessment of Lipid Peroxidation in Experimental Edematous and Necrotizing Rat Pancreatitis," Pancreas 14:350–354 (1997).

Lieberman et al., "Anabolic Effects of Recombinant Insulin–Like Growth Factor–I in Cachectic Patients with the Acquired Immunodeficiency Syndrome," J. Clin. Endo. Meta. 78:404–410 (1994).

Lifschitz et al., "A Carbon–13 Breath Test to Characterize Glucose Absorption and Utilization in Children," J. Ped. Gastro. and Nutr. 7:842–847 (1988).

Lifschitz et al., "[$^{13}$C] Acetate Oxidation in Infants After Oral Versus Rectal Administration: A Kinetic Model," J. Ped. Gastro. Nutr. 4:699–706 (1985).

Lobo et al., "In Situ Microassay of Ornithine Decarboxylase," Analytical Biochemistry 238:95–98 (1996).

Loser et al., "$^{13}$C–Starch Breath Test—Comparative Clinical Evaluation of an Indirect Pancreatic Function Test," Z Gastroentrol 35:187–194 (1997).

Loser et al., "Comparative Clinical Evaluation of the $^{13}$C–Mixed Triglyceride Breath Tests as an Indirect Pancreatic Function Test,".

Maes et al., "$^{13}$C–Octanoic Acid Breath Test for Gastric Emptying Rate of Solids," Gastroentrology 114:856–859 (1998).

Maes et al., "Gastric Emptying of the Liquid, Solid and Oil Phase of a Meal in Normal Volunteers and Patients with Billroth II," Gastrojejunostomy, 28:197–204 (1998).

Maes et al., "Gastric Emptying Rate of Solids in Patients with Nonulcer Dyspepsia," Dig. Dis. and Sci. 42:1158–1162 (1997).

Maes et al., "Influence of Octreotide on the Gastric Emptying of Solids and Liquids in Normal Healthy Subjects," Alimert Pharmacol. Ther. 9:11–18 (1995).

Manolis et al., "The Diagnostic Potential of Breath Analysis," Clin. Chem. 29:5–15 (1983).

Marchini et al., "Phenalylalaine Conversion to Tyrosine: Comparative Determination with L-[Ring-$^2$H$_5$] Phenylaline and L-[1-$^{13}$C]Phenylalaine as Tracers in Man," Metabolism 42:1316–1322 (1993).

Martins et al., "A $^{13}$CO$_2$ Breath Test to Assess the Metabolism of Triglyceride–Rich Lipoprotein Remnants in Mice," J. Lipid Research 39:691–698 (1998).

Matsumoto et al., "[$^{13}$C] Methacetin Breath Test for Evaluation of Liver Damage" Dig. Dis. and Sci. 32:344–348 (1987).

McClean et al., "Bile Salt–Stimulated Lipase and Digestion of Non–Breast Milk Fat" J. Pedr. Gastro and Nutr. 26:39–42 (1998).

Meister et al., "[52] γ–Glutamylcyclotransferase from Rat Kidney," Methd Enzym. 113:438–445 (1985).

Metges et al., "Medium– and Long–Chain Triglycerides Labeled with $^{13}$C: A Comparison of Oxidation After Oral or Parenteral Administration in Humans," Am. Inst. Nutr. 0022:31–36 (1990).

Michaletz et al., "Assessment of Mitochondrial Function In Vivo with a Breath Test Utilizing α–Ketoisocaproic Acid" Heptaology 10:829–832 (1989).

Mion et al., "Human Hepatic Macrovesicular Steatosis: A Non invasive Study of Mitrochondiral Ketoioscaproic Acid Decarboxylation" Metabolism 44:699–700 (1995).

Mion et al., "Aminopyrine Breath Test: Development of a $^{13}$C–Breath Test for Quantitative Assessment of Liver Function in Humans," Hepato–Gastroenterology 42:931–938 (1995).

Miyakawa et al., "Estimation of Fat Absorption with the $^{13}$C–Trioctanoin Breath Test after Pancreeatoduodenectomy or Pancreatic Head Resection," World J. Surg. 20:1024–1029 (1996).

Mohan et al., "$^{13}$CO$_2$ Washout Kinetics in Acute Hypercapnia," Respiration Phsiol. 86:159–170 (1991).

Motil et al., "Leucine Oxidation Changes Rapidly after Dietary Protein Intake is Altered in Adult Women but Lysine Flux is Unchanged as is Lysine Incorporation into VLD-L–Apolipoprotein B–100," Amer. Inst. Nutr. 3166:41–51 (1993).

Mossi et al., "Gastric Emptying of Liquid Meals Measured Noninvasively in Humans with [$^{13}$C]Acetate Breath Test," Dig. Dis. Sci 39:107S–109S (1994).

Moulton–Barrett et al., "Serum $^{13}$C–Bicarbonate in the Assessment of Gastric Helicobacter pylori Urease Activity," Am. J. Gastroent. 88:369–374 (1993).

Mudambo et al., "Gastric Emptying in Soldiers During and After Field Exercises in the Heat Measured with the [$^{13}$C] acetate Breath Test Method," Eur. J. App. Physiol. 75:109–114 (1997).

Muller et al., "Investigation of Cardiac Metabolism Using Stable Isotopes and Mass Spectrometry," Basis Res. Cardio. 88:272–281 (1993).

Murray et al., "An Assay for Paracetmol, Produced by the O–Deethylation of Phenacetin in vitro, Using Gas Chromotography/Electron Capture Negative Ion Chemical Ionization Mass Spectrometry," Biomed. Envir. Mass Spec. 13:91–93 (1986).

Murphy et al., "Gastrointestinal Handling of [1–$^{13}$C]palmitic Acid in Healthy Controls and Patients with Cystic Fibrosis," Arch. Dis. Child. 76:425–427 (1997).

Murphy et al., "The Gastrointestinal Handling and Metabolism of [1–$^{13}$C]palmitic Acid in Healthy Women," Lipids 30:291–298 (1995).

Pallikarakis et al., "$^{13}$CO$_2$ Breath Test Methodology in the Study of Glucose Metabolism in Man." Rec. Dev. Mass Spec. Biochem. Med. 6:163–172 (1980).

Pfaffenbach et al., "Noninvasive $^{13}$C–octanoic Acid Breath Test for Measurement of Solid Gastric Emptying—Comparison to Scintigraphy in Diabetes and Reproducibility in Healthy Volunteers," Z Gastroenterol 33:141–145 (1995).

Phillips et al., "Breath Tests in Medicine," Scientific American Jul. (1992).

Pont et al., "Isotope Ratio Mass Spectrometry, Compared with Conventional Mass Seectrometry in Kinetic Studies at Low and High Enrichment Levels: Application to Lipoprotein Kinetics," Analytical Biochem. 248:277–287 (1997).

Quantz et al., "Evidence for Increased Microsomal Hepatic Functions in Thalassemic Children as Detected by [$^{13}$C] aminopyrine Breath Test," 29:111–116 (1993).

Radke et al., "Tracer Kinetic Studies on a Methionine–Supplemented Soy–Based Infant Formula Using 1–$^{13}$C– and $^{15}$N–Methionine as Tracers," *J. Pediatr. Gastroent. and Nutr.* 21:209–214 (1995).

Raguso et al., "Effect of Cystine Intake on Methionine Kinetics and Oxidation Determined with Oral Tracers of Methionine and Cysteine in Healthy Adults," *Am. J. Clin. Nutr.* 66:283–292 (1997).

Rating et al., "Breath Tests: Concepts, Applications and Limitations," *Eur. J. Pediatr* 156:S18–S23 (1997).

Rocker et al., "Breath–by–Breath Measurements for the Analysis of Exogenous Glucose Oxidation During Intense Endurance Exercise Using [$^{13}$C]–Isotopes," *Int. J. Sports Med.* 17:480–486 (1996).

Rost et al., "Increase of Cytochrome P450IA2 Activity by Omerprazole: Evidence by the $^{13}$C–[N–3–methyl]–caffeine Breath Test in Poor and Extensive Metabolizers of S–Mephenytoin," *Clin. Pharmacol Ther.* 52:170–180 (1992).

Rothenbacher et al., "Dyspepsia in Relation to *Helicobacter pylori* Infection and Psychosocial Work Stress in White Collar Employees," *Amer. J. Gastroent.* 93:1443–1449 (1998).

Rothenbacher et al., "History of Antibiotic Treatment and Prevalence of *H. pylori* Infection Among Children: Results of a Population–Based Study," *J. Clin. Epidemol.* 51:267–271 (1998).

Rothenbacher et al., "Prevalence and Determinants of *Helicobacter pylori* Infection in Preschool Children: A Population–based Study From Germany," *Int. J. Epid.* 27:135–141 (1998).

Russell–Jones et al., "The Use of Isotopes to Unravel the Hyperlipidemia of Adult Growth Hormone Deficiency," *Horm. Res.* 48:111–115 (1997).

Saccomani et al., "Bicarbonate Kinetics in Humans: Identification and Validation of a Three–Compartment Model," *Amer. Phsiol. Soc.* 0193:E183–E192 (1995).

Santhosh–Kumar et al., "Measurement of Excitatory Sulfur Amino Acids, Cysteine Sulfinic Acid, Cysteic Acid, Homocysteine Sulfinic Acid, and Homocysteine Acid in Serum by Stable Isotope Dilution Gas Chromatrography–Mass Spectrometry and Selected Ion Monitoring," *Analytical Biochemistry* 220:249–256 (1994).

Sarker et al., "Prevalence of *Helicobacter pylori* Infection in Infants and Family Contacts in a Poor Bangladesh Community," *Dig. Dis. Sci.* 40:2669–2672 (1995).

Sastry et al., "Volatiles Emitted by Humans," *Biochem. Appl. Mass Spec.* Cahpter 34 II:1085–1129 (1980).

Schadewaldt et al., "Application of Isotope–selective Nondispersive Infrared Spectrometry (IRIS) for Evaluation of [$^{13}$C]octanoic Acid Gastric–Emptying Breath Tests: Comparison with Isotope Ratio–Mass Spectrometry (IRMS)," *Clin. Chem.* 43:518–522 (1997).

Schadewaldt et al., "Metabolism of Branched–Chain Amino Acids in Maple Syrup Urine Disease," *Eur. J. Pediatr.* 156:S62–S66 (1997).

Schadewaldt et al., "Leucine Oxidation In Vivo: Inter– and Intraindividual Variation in Healthy Subjects as Assessed by Oral L–[1–$^{13}$C]Leucine Loads," *Isotop. Envir. Hlth. Stud.* 30:141–150 (1994).

Schneider et al., "Validation of $^{13}$CO$_2$ Breath Analysis as a Measurement of Demethylation of Stable Isotope Labeled Aminopyrine in Man," *Clinica Chimica Acta* 84:153–162 (1978).

Schoeller et al., "Fecal $^{13}$C Analysis for the Detection and Quantitaion of Intestinal Malabsorption," *J. Clin. Lab. Med.* 97:439–448 (1981).

Shreeve et al., "Test for Alcoholic Cirrhosis by Conversion of [$^{14}$C] or [$^{13}$C]Galactose to Expired CO$_2$," *Gastroentrology* 71:98–101 (1976).

Sidossis et al., "A New Collection Factor for Use in Tracer Estimations of Plasma Fatty Acid Oxidation," *Amer. Physiol. Soc.* 0193:E649–E656 (1995).

Simenhoff et al., "Biochemical Profile of Uremic Breath," *New Eng. J. Med.* 297:131–135 (1997).

Solomons et al., "Application of a Stable Isotope ($^{13}$C)–labeled Glycocholate Breath Test to Diagnosis of Bacterial Overgrowth and Ileal Dysfunction," *J. Clin. Lab. Med.* 90:431–439 (1997).

Springfield et al., "Pitfalls in the Use of Breath Pentane Measurements to Assess Lipid Peroxidation," *J. Lip. Res.* 35:1497–1504 (1994).

Srivenugopal et al., "Activity and Distribution of the Cysteine Prodrug Activating Enzyme, 5–Oxo–L–Prolinase, in Human Normal and Tumor Tissue," *Cancer Letters* 117:105–111 (1997).

Storch et al., "Quantitative Study In Vivo of Methionine Cycle in Humans Using [methyl–$^2$H$_3$]– and [1–$^{13}$C]methionine," *Amer. Phsiol. Soc.* 1849:E322–E331 (1988).

Swart et al., "$^{13}$C Breath Tests in Gastroentrological Practice," *Scand. J. Gastroentrol.* 225:13–18 (1998).

Swart et al., "Evaluation Studies of the $^{13}$C–Mixed Triglyceride Breath Test in Healthy Controls and Adult Cystic Fibrosis Patients with Exocrine Pancreatic Insufficiency," *Digestion* 58:415–420 (1997).

Taniguchi et al., "Simple $^{13}$C–Urea Breath Test with Infra––Red Spectrophotometer," *J. Gastroent.* 31:37–40 (1996).

Turgeon et al., "Prediction of Interpatient and Intrapatient Variation in OG 37–325 Dosing Requirements by the Erythromycin Breath Test," *Transplantation* 57:1736–1741 (1994).

Turkalj et al., "Effect of Increasing Doses of Recombinant Human Insulin–Like Growth Factor–I on Glucose, Lipid, and Leucine Metabolism in Man," *J. Clinc. Endocrin. Metabol.* 75:1186–1191 (1992).

Van–Gossum et al., "Assessment of Lipid Peroxidation in Humans by Breath Pentane Output Measurement," *Acta Gastroent Belgica* LV:245–248 (1992).

Van–Der–Werf et al., "Enzymatic Conversion of 5–Oxo–L–Proline to L–Glutamate Coupled with Cleavage of Adenosine Triphosphate to Adenosine Diphosphate, a Reaction in the γ–Glutamyl Cycle," *Proc. Nat. Acad. Sci.* 68:2982–2985 (1971).

Vann et al., "The Detoxifying Liver Cytochromes: A Non–invasive Method for their Continuous Measurement in Individual Rats," *Proc. West. Pharmacol. Soc.* 20:91–95 (1977).

Veereman–Wauters et al., "The $^{13}$C–Octanoic Acid Breath Test: A Non–invasive Technique to Assess Gastric Emptying in Preterm Infants," *J. Pediatr. Gastroent. Nutr.* 23:111–117 (1996).

Veerkamp et al., "$^{14}$CO$_2$ Production Is No Adequate Measure of [$^{14}$C] Fatty Acid Oxidation," *Biochem. Med. Metabol. Biol.* 35:248–259 (1986).

Ventrucci et al., "$^{13}$C Labelled Cholesteryl Octanoate Breath Test for Assessing Pancreatic Excorine Insufficiency," *Gut* 42:81–87 (1998).

Verhoeven et al., "Stable Isotope Studies of Phytanic Acid α–Oxidation: In Vivo Production of Formic Acid," *Eur. J. Pediatr.* 156:S83–S87 (1997).

Verges et al., "In Vivo Metabolism of Apolipoportien A–IV In Severe Hypertriglyceridemia: A Combined Radiotracer and Stable Isotope Kinetic Study," *J. Lipid Res.* 35:2280–2291 (1994).

Watkins et al., "Diagnosis and Differentiation of Fat Malabsorption in Children Using 13C–Lableled Lipids: Trioctanoin, Triolein, and Palmitic Acid Breath Tests," *Gastroentrology* 82:911–917 (1982).

Watkins et al., "Erythromycin Breath Test as an Assay of Glococorticoid–Inducible Liver Cytochromes P–450," *J. Clin. Invest.* 9738:688–697 (1989).

Welle et al., "Increased Protein Turnover in Obese Women," *Metabolism* 9:1028–1034 (1992).

Wendel et al., "Hydrocarbon Exhalation," *Meth. Enzy.* 77:10–15 (1981).

Wolfe et al., "Clinical Applications of Stable Isotope," *Tracers in Metabolic Research,* Chapter 15 (1994).

Wolfe et al., "Isotopic Measurement of Glucose and Lactate Kinetics," *Annals Med.* 22:163–170 (1990).

Wutzke et al., "Evaluation of Oro–coecal Transit Time: A Comparison of the Lactose–[$^{13}$C,$^{14}$N]uride $^{13}$CO$_2$ and the Lactulose H$_2$–Breath Test in Humans." *Eur. J. Clin. Nutr.* 51:11–19 (1997).

Wutzke et al., "Gastric Emptying and Intestinal Retention Time in Two Different Breakfast Versions: A Combined Sodium–[$^{13}$C]acetate/lactose–[$^{13}$C]ureide–breath Test Study," *Z Ernahrungswiss* 36:372 (1997).

Zello et al., "Dietary Lysine requirements of Young Adult Males Determined by Oxidation of L–[1–$^{13}$C]phenylalanine," *Amer. Physiol. Soc.* 1849:E677–E685 (1993).

Ziegler et al., "[$^{13}$C]Octanoic Acid Breath Test for Non–Invasive Assessment of Gastric Emptying in Diabetic Patients: Validation and Relationship to Gastric Symptoms and Cardiovascular Autonomic Function," *Diabetologia* 39:823–830 (1996).

Q.R. Rogers, et al., "In Vivo Synthesis and Utilization of Arginine in the Rat", Jul. 1972, American Journal of Physiology, vol. 223, No. 1, pp. 236–240.

J. Harmeyer, et al., "The Metabolic Conversion of Arginine in the Rumen Wall and its Importance in Ruminant Nitrogen Metabolism", 1967, Isotope Stud, Nitrogen Chain, Proc. Symp., Vienna, vol., pp. 265–274.

A. A. Elizian—& Biol., Zh, Arm., vol. 37, No. 5, pp. 416–419.

L.S. Arutyunyan, et al., "Effect of Thyroid Hormones on Liver Arginase Activity of Rats", Sep. 24, 1984, Chemical Abstracts, vol. 101, No. 13.

Paul R. Tramell, et al., "Arginine and Urea Metabolism in the South American Land Snail, Strophocheilus Oblongus", 1972, Comp. Biochem. Physiol., vol. 42B, pp. 439–449.

Ewa Birkner, et al., "The Influence of Hyperthermia on Ornithine Carbamolytransferase and Arginase Activity in Liver or Rats", 1991, Ann. Acad. Med Silesiensis, vol. 24, pp. 13–17.

Joyce A. Nettleton, et al., "Reutilization of guanido–labeled Arginine in Rat Liver Proteins and the Influence of Diets", 1974, J. Nutr., vol. 104, No. 7, pp. 916–921.

Olivier Levillain, et al., "Production of Urea from Arginine in Pars Recta and Collecting Duct of the Rat Kidney", 1989, Renal Physiol. Biochem., vol. 12, No. 5–6, pp. 302–312.

Deliane Klein, et al., "Increased Arginase Activity During Lymphocyte Mitogenesis" Mar. 15, 1978, Biochem., Biophys. Res. Commun., vol. 81, No. 1, pp. 119–204.

H. Nishibe, "Ultramicromethod for the Determination of Human Arginase in the Presence of Urea", Sep. 20, 1976, Clin. Chim. ACTA, vol. 71, No. 3 pp. 413–418.

T.U. Ruegg, et al., "A Rapid and Sensitive Assay for Arginase", 1980, Analytical Biochemistry, vol. 102, No. 1, pp. 206–212.

M. Snejdarkova, et al., "Model of Arginine Dynamics in the Japanese Quail . . . Changes in Selected Compartments", 1983, Nutrition Reports International, vol. 38, No. 4, pp. 753–760.

H. Pratzel, et al., "Biochemistry of free Amino Acids in the . . . I. Die Arginase–Reaktion", Archives of Dermatological Res., DE, Springer, International, Berlin, vol. 259, No. 2, pp. 151–156.

F.G. Carl, et al., "Manganese and Epilepsy: Brain Glutamine Sythetase and Liver Arginase Activities in Genetically Epilepsy Prone and Chronically Seizured Rats", 1993, Epilepsia, US, Raven Press Ltd., NY., vol. 34, No. 3, pp. 441–446.

\* cited by examiner

The γ-glutamyl cycle.
(From Meister, Science 180 : 33-39, 1973)

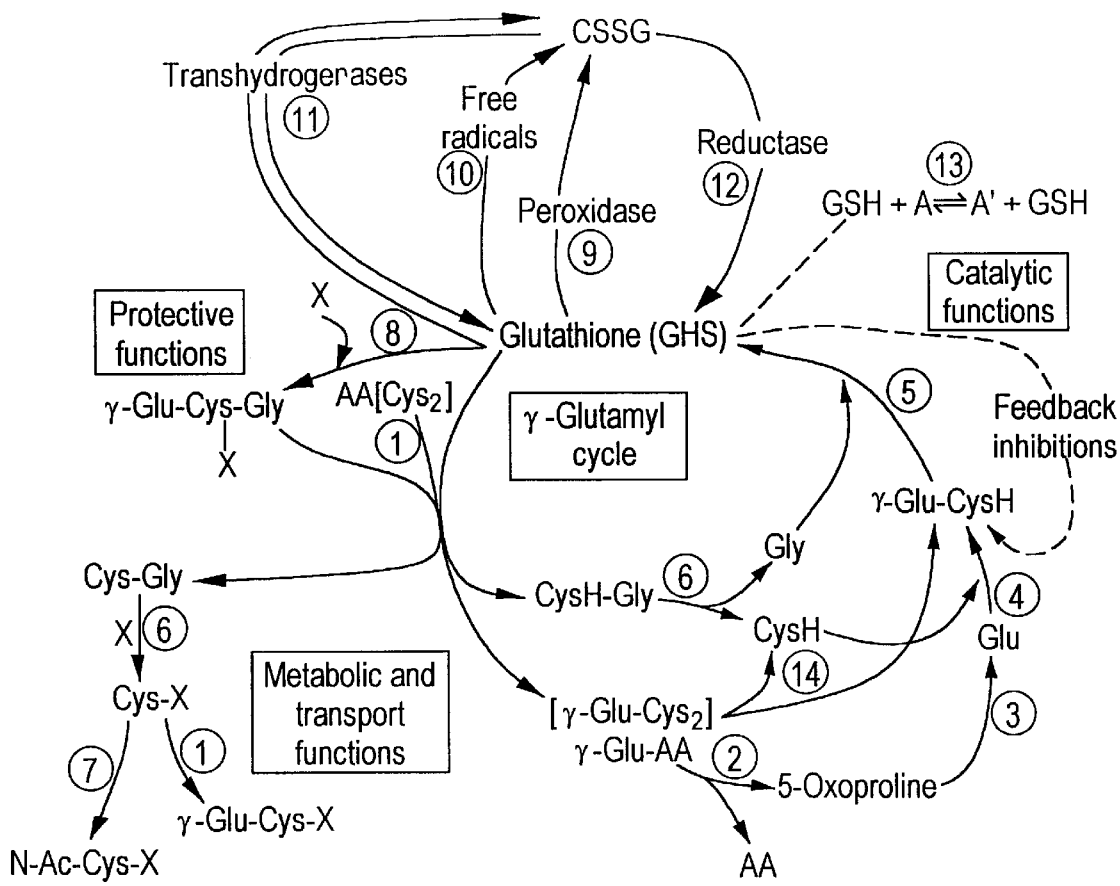

Overview of the metabolism and function of glutathione. (1) γ-Glutamyltranspeptidase; (2) γ-glutamylcyclotransferase; (3) 5-oxoprolinase; (4) γ-glutamilcysteine synthetase; (5) glutathione synthetase; (6) dipeptidase; (7) L-cysteine- S-conjugate N-acetyltransferase; (8) glutathione S-transferases; (9) glutathione peroxidase; (10) presumably nonenzymatic; (11) glutathione transhydrogenases, e.g., enzymes that catalyze thiol-protein reactions; (12) glutathione disulfide reductase; (13) reactions in which glutathione is required, but not consumed, such as those catalized by formaldehyde dehydrogenase, glyoxylase, maleylacetoacetate isomerase, DDT-dehydrochlorinase, and prostaglandin endoperoxidase isomerases; (14) transport and reduction of γ-glutamylcystine (AA = amino acids; X = compounds that form conjugates with glutathione). (Taken from Holmgren, A., Branden, C-I., Jornvall, H., and Sjoberg, B-M.; Eds.; "Thioredoxen and Glutaredoxin Systems: Structure and Function" Raven Press; New York, 1986, p. 340.)

FIGURE 1b
PRIOR ART

The interrelationships between arginine, urea cycle intermediates, polyamines, creatine, nitric oxide (NO) and proline. Slight modification of Fig. 19-2 in Valle and Simell (1995). The hyperornithenemies. In The Metabolic Basis of Inherited Disease, Vol. 1 (C. R. Scriver, A. L. Beaudet, W. S. Sly and D. Valle Eds.), pp. 1147-1186. New York: McGraw-Hill.

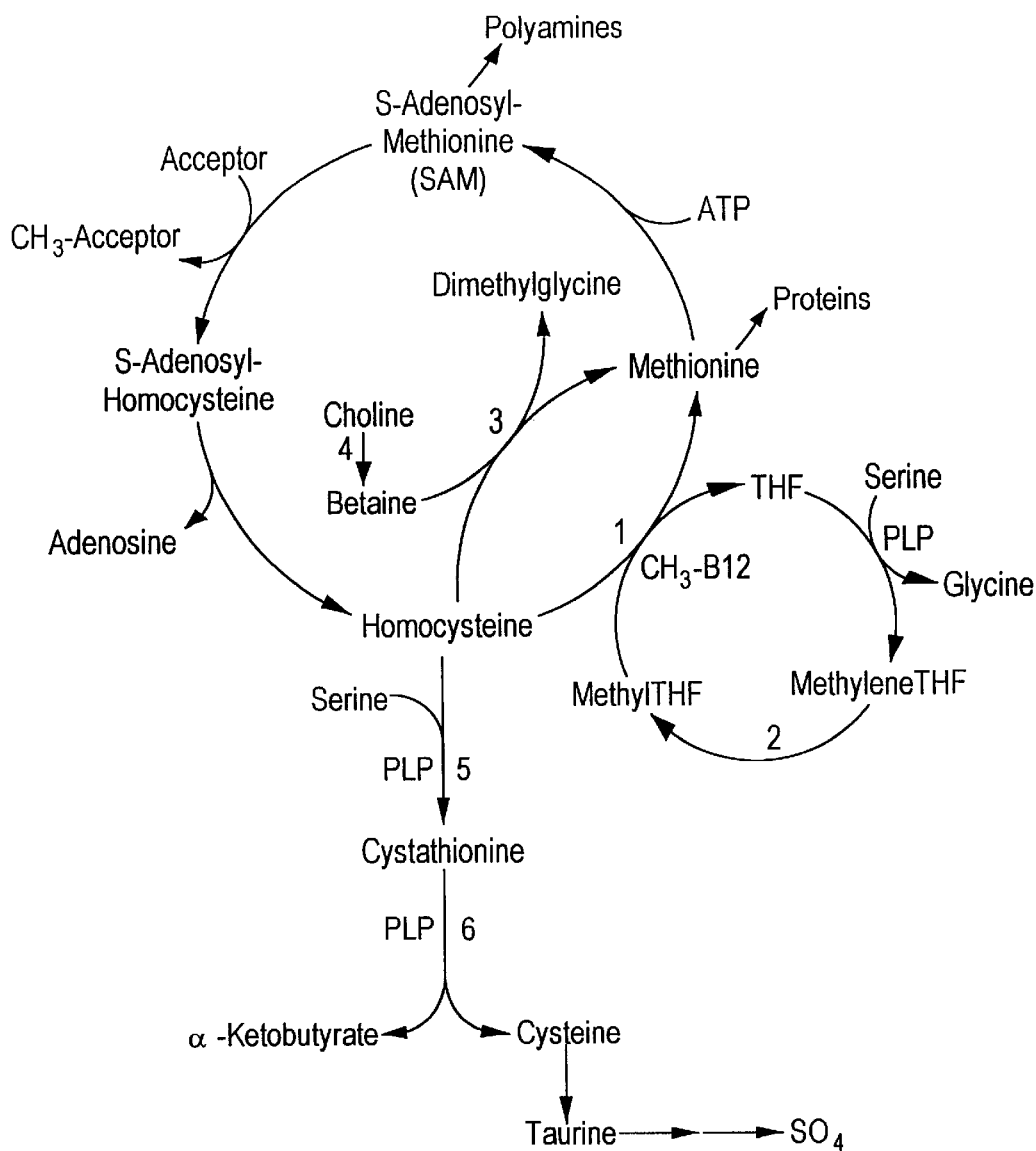

Homocyst(e)ine metabolism in humans and animals. Enzymes: 1, $N$-5-methyltetrahydrofolate:homocysteine methyltransferase; 2, methylenetetrahydrofolate reductase; 3, betaine:homocysteine methyltransferase; 4, choline dehydrogenase; 5 cystathionine β-synthase; 6,δ -cystathionase. THF, tetrahydrofolate; PLP, pyridoxal 5'-phosphate; ATP, adenosine 5'-triphosphate; B12, vitamin B . (adapted from J. Selhub and J.W. Miller. Am J Clin Nutr 1992;55;131-8)

FIGURE 3
PRIOR ART

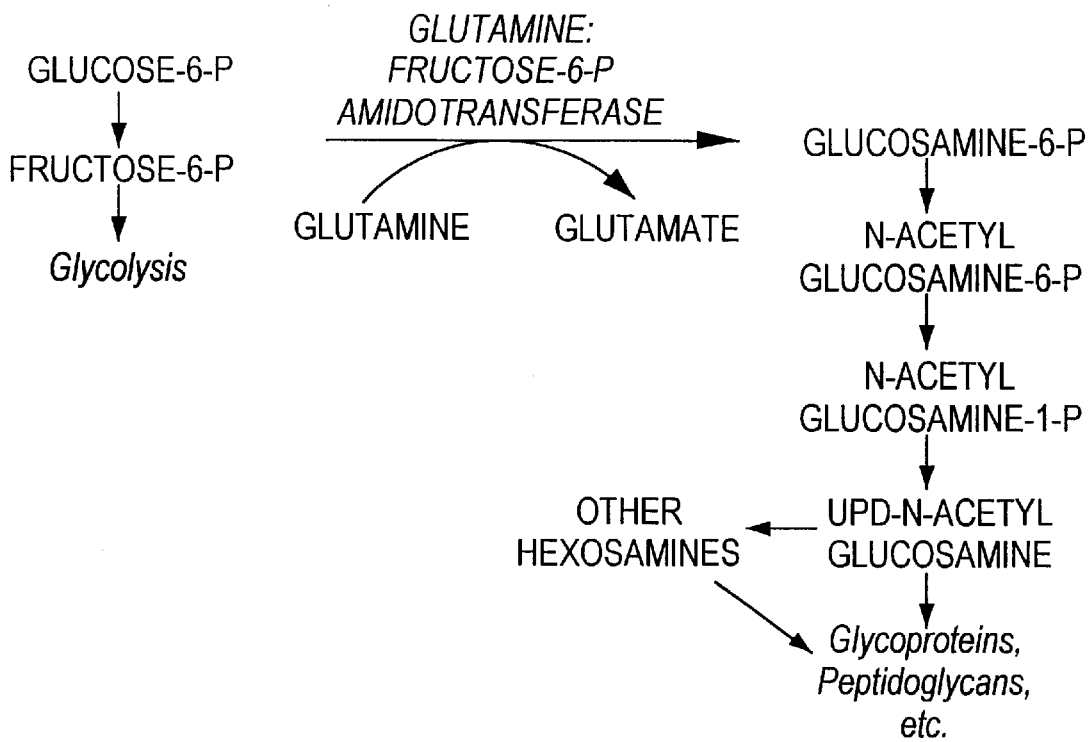
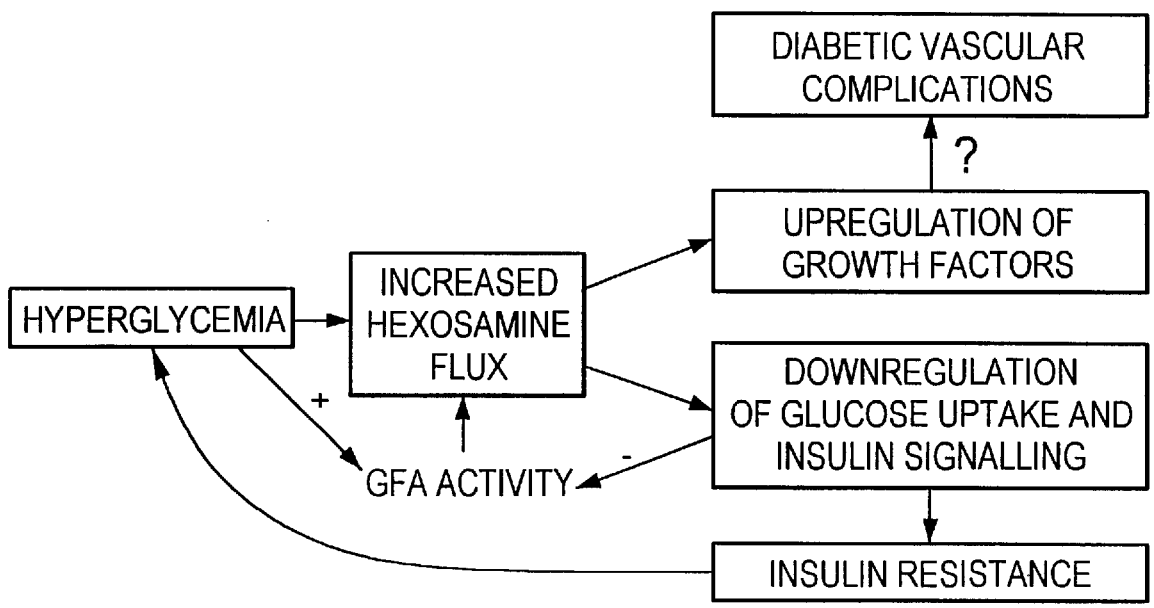
(From McClain et al., Hexosamines and Insulin Resistance; DIABETES, Vol 45, August 1996.)
FIGURE 4
PRIOR ART

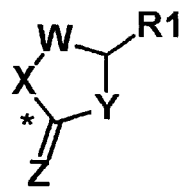

R1 = carboxyl, carboxylamide, and ketone functional groups described in Table IV, with characteristic reversible subfunctionalities, including as preferred:

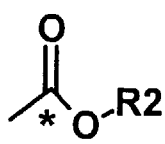 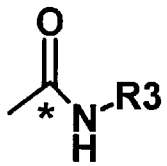 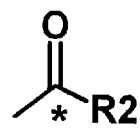

X = N, O, S

Y = N, O, S

W = CH2, CH-alkyl, CH-aryl, CH2CH2, CH2-CH-alkyl, CH2-CH-aryl

R2 = H, methyl, ethyl, propyl, butyl, pentyl, hexyl, isopropyl, isobutyl, sec-butyl tert-butyl, isopentyl, isohexyl, phenyl, phenylmethyl, etc.; or R3 = H, methyl, ethyl, propyl, butyl, pentyl, hexyl, isopropyl, isobutyl, sec-butyl tert-butyl, isopentyl, isohexyl, phenyl, phenylmethyl, etc.; or

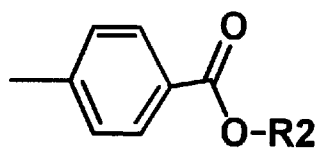

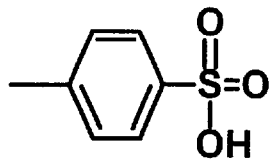

* = Preferred position of isotopic release tag in tracer core

FIGURE 5

Oxiprolinase Metaprobes

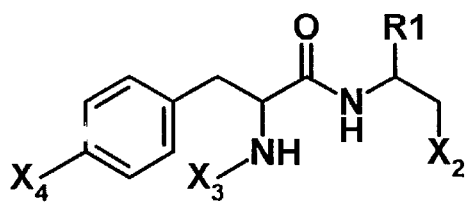

R1 = carboxyl, carboxylamide, and ketone functional groups described in Table IV, with characteristic reversible subfunctionalities, including as preferred:

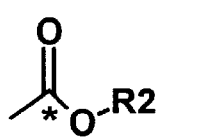 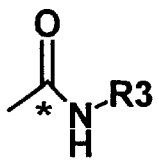 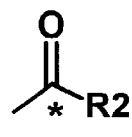

X2, R2 = H, methyl, ethyl, propyl, butyl, pentyl, hexyl, isopropyl, isobutyl, sec-butyl tert-butyl, isopentyl, isohexyl, phenyl, phenylmethyl, etc.

X3 = acetyl, benzoyl, benzyloxycarbonyl, t-butoxycarbonyl, hippuryl, methoxyacetyl, methoxycarbonyl, pivaloyl, etc.

R3 = H, methyl, ethyl, propyl, butyl, pentyl, hexyl, isopropyl, isobutyl, sec-butyl tert-butyl, isopentyl, isohexyl, phenyl, phenylmethyl, etc.; or

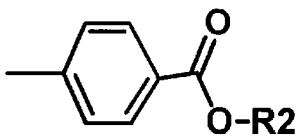

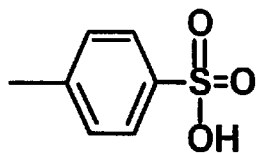

X4 = H, OH, NH$_2$, OCH$_3$

* = Preferred position of isotopic release tag in tracer core

Figure 7

Chymotrypsin Metaprobes

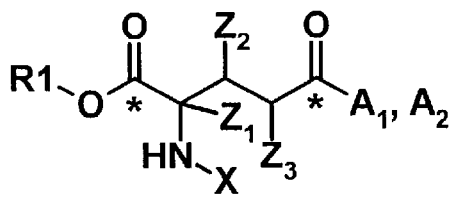

R1 = carboxyl functional groups described in Table IV, with characteristic reversi subfunctionalities, including as preferred esters, methyl, ethyl, propyl, butyl, pent hexyl, isopropyl, isobutyl, sec-butyl, tert-butyl, isopentyl, isohexyl, phenyl, phenylmethyl etc.

A1 = 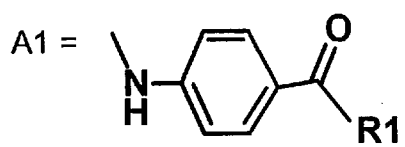

A2 = 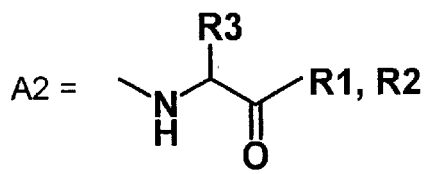

R2 = 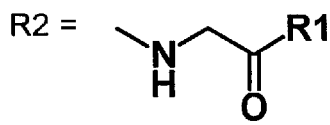

R3 = CH2-SH, CH2-S-CH3, methyl, ethyl, propyl, butyl, pentyl, hexyl, isoprop isobutyl, sec-butyl, tert-butyl, isopentyl, isohexyl, phenyl, phenylmethyl, X = acetyl, benzoyl, benzyloxycarbonyl, t-butoxycarbonyl, hippuryl, methoxyacetyl, methoxycarbonyl, pivaloyl, etc.

* = Preferred position of isotopic release tag in tracer core

Figure 8
Glutamyl Transpeptidase Metaprobes

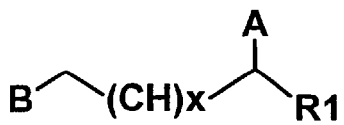

R1 = carboxyl, carboxylamide, and ketone functional groups described in Table IV, with characteristic reversible subfunctionalities, including as preferred:

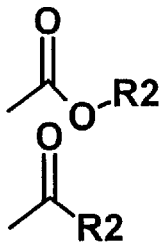

R2 = H, methyl, ethyl, propyl, butyl, pentyl, hexyl, isopropyl, isobutyl, sec-butyl tert-butyl, isopentyl, isohexyl, phenyl, phenylmehyl, etc.; or

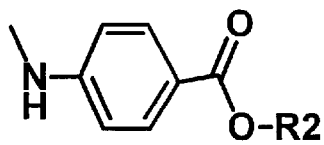

A = 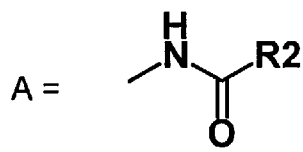

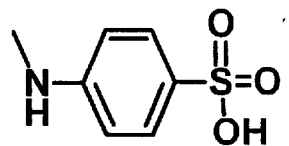

B = 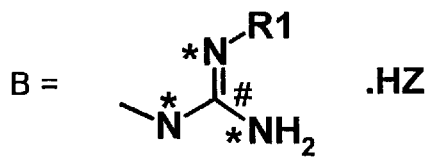

X = 1 or 2

Z = halide, mesylate, tosylate

, * = Preferred position of isotopic release tag in tracer core

FIGURE 10

Nitric Oxide Synthase Metaprobes

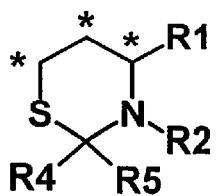 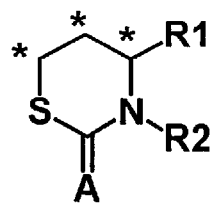

R1 = carboxyl, carboxylamide, and ketone functional groups described in Table IV, with characteristic reversible subfunctionalities, including as preferred:

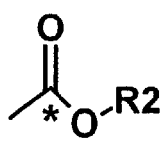 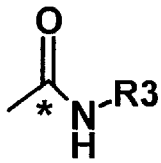 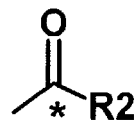

R2 = H, methyl, ethyl, propyl, butyl, pentyl, hexyl, isopropyl, isobutyl, sec-butyl tert-butyl, isopentyl, isohexyl, phenyl, phenylmethyl, etc.; or R3 = H, methyl, ethyl, propyl, butyl, pentyl, hexyl, isopropyl, isobutyl, sec-butyl tert-butyl, isopentyl, isohexyl, phenyl, phenylmethyl, etc.; or

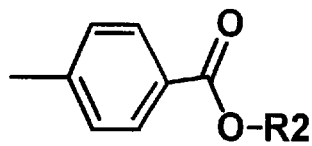

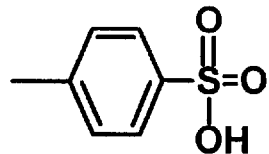

R4 = -OH, -SH, -C≡N, -NHR2, -N(R2)$_2$; or R4

R5 = H, methyl, ethyl, propyl, butyl, pentyl, hexyl, isopropyl, isobutyl, sec-butyl tert-butyl, isopentyl, isohexyl, etc.

A = NH, O, S

\* = Preferred position of isotopic release tag in tracer core

Figure 11a

Cystathionine Synthase Metaprobes (Part 1)

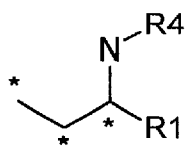

R1 = carboxyl, carboxylamide, and ketone functional groups described in Table IV, with characteristic reversible subfunctionalities, including as preferred:

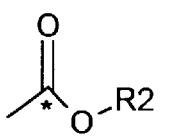 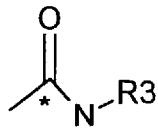 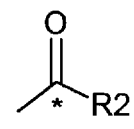

R2 = H, methyl, ethyl, propyl, butyl, pentyl, hexyl, isopropyl, isobutyl, sec-butyl tert-butyl, isopentyl, isohexyl, phenyl, phenylmethyl, etc.; or R3 = H, methyl, ethyl, propyl, butyl, pentyl, hexyl, isopropyl, isobutyl, sec-butyl tert-butyl, isopentyl, isohexyl, phenyl, phenylmethyl, etc.; or

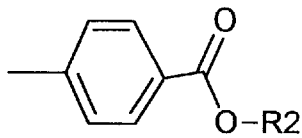

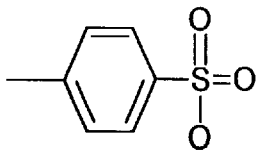

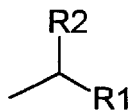

R4 = H, formyl, acetyl, benzoyl, benzyloxycarbonyl, t-butoxycarbonyl, hippuryl, methoxyacetyl, methoxycarbonyl, pivaloyl, etc.

* = Preferred position of isotopic release tag in tracer core

Figure 11b

Cystathionine Synthase Metaprobes (Part 2)

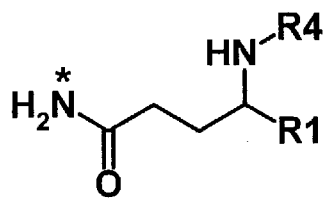

R1 = carboxyl, carboxylamide, and ketone functional groups described in Table IV, with characteristic reversible subfunctionalities, including as preferred:

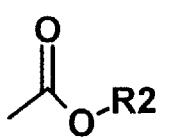 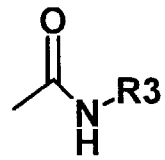 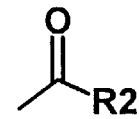

R2 = H, methyl, ethyl, propyl, butyl, pentyl, hexyl, isopropyl, isobutyl, sec-butyl tert-butyl, isopentyl, isohexyl, phenyl, phenylmethyl, etc.; or R3 = H, methyl, ethyl, propyl, butyl, pentyl, hexyl, isopropyl, isobutyl, sec-butyl tert-butyl, isopentyl, isohexyl, phenyl, phenylmethyl, etc.; or

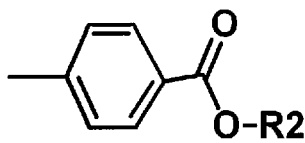

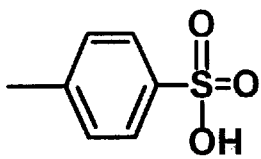

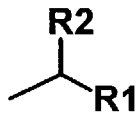

R4 = H, formyl, acetyl, benzoyl, benzyloxycarbonyl, t-butoxycarbonyl, hippuryl, methoxyacetyl, methoxycarbonyl, pivaloyl, etc.

* = Preferred position of isotopic release tag in tracer core

Figure 12a

Glutamine Fructose-6-phosphate
Amidotransferase Metaprobes (Part 1)

R1 = H, formyl, acetyl, benzoyl, benzyloxycarbonyl, t-butoxycarbonyl, hippuryl, methoxyacetyl, methoxycarbonyl, pivaloyl, etc.

* = Preferred position of isotopic release tag in tracer core

Glutamine Fructose-6-phosphate
Amidotransferase Metaprobes (Part 2)

IN VIVO DETERMINATION OF METABOLIC FUNCTION FOR USE IN THERAPY MANAGEMENT

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The economic and social burden to society of managing a number of costly human medical problems, including digestive disorders, cancer, critical care, infectious diseases, atherosclerosis and neurodegenerative disorders, is severe. Historically, clinicians have tried different ways to assess the status of a patient and monitor the effectiveness of therapy. For example, it has been recognized since antiquity that the monitoring of breath is desirable, as it contains clues to many diseases and metabolic processes in the body.

Breath tests are useful, specifically, as non-invasive procedures for the detection of isotopically labelled tracer substrates, particularly the stable carbon isotope $^{13}C$. Breath test tracer substrates may be given orally, no blood need be drawn and samples may be collected easily.

Historically, tracers have been used in diverse scientific settings to follow the metabolic fate of tracer- labelled molecules in dynamic systems, e.g., to determine rates of synthesis, transformation or degradation of molecules in vivo, in intact organisms or perfused organs, or in vitro, with tissue homogenates or subcellular fractions.

The most commonly used tracers are radioactive, e.g., $^{3}H$, 14C or $^{32}P$-labelled molecules. These can be "traced" by measuring the intensity and location of the radiation emanating from the tracers as a function of time. Non-radioactive nuclides, or stable isotopes such as $^{13}C$ can also be used advantageously as tracers, especially in metabolic studies. Stable isotope tracers can be "traced" by examining the properties of their molecular mass as it becomes diluted over time by the natural abundance masses also contained within the biological matrix under study in the tracer experiment.

The most frequent approach for using tracers is to incorporate a desired nuclide atom into a target molecule whose transformation is to be studied as a function of time, and then to follow the metabolic fate of the molecule as it undergoes one or more biological interconversions. Another approach, used more in determining properties of enzyme systems, focuses on determining the rate at which the nuclide disappears from the tracer labelled molecule and then reappears after incorporation into biological variants of the initial molecule, e.g., metabolites.

The analysis of nuclide labeling patterns and the quantitation of tracer rates of appearance and disappearance are often time consuming and technically complex operations. For example, while enzymology in vitro can be extensively manipulated so as to minimize the confounding effects of biochemical recycling and of metabolic integration on the calculation of pertinent kinetic parameters, far fewer possibilities exist for similar manipulations in vivo.

Another drawback in the historic application of labelled tracer probes is that easy, non-invasive determinations such as breath tests are often not possible, and, as such, invasive methods like biopsy may need to be used. Although breath tests have been shown to be useful in conjunction with determinations of hepatic function and enzyme induction, gastric emptying, maldigestion/malabsorption, and intermediary metabolism, one notable disadvantage or limitation of the breath test for disease diagnosis is that while the labelled end product can be measured, e.g., $^{13}CO_2$, this does not provide information on various pools and fluxes the labelled substrate and its metabolites pass through, in order to give an indication of the presence or absence of a disease condition.

It would, therefore, be beneficial to the art of utilizing tracers in therapy management to systematize and streamline their design and application, especially for the purpose of determining the status of processes critical to the maintenance of normal function in the context of health and disease in vivo, without the drawbacks mentioned above.

SUMMARY OF THE INVENTION

It is an object of the present invention to provide in vivo analytical methods that allow for diagnosis and management of therapy for diseases involving discrete biochemical pathways. In the method of the invention, a labelled tracer probe, a specifically designed substrate of a "gateway" enzyme, an enzyme marking a regulatory point in a discrete biochemical pathway, is administered to a subject; a labelled product of the action of the enzyme is measured; and the appearance and concentration of the product are related to the disease condition of interest. Determination of the rate of substrate-product conversion of the gateway enzyme allows for the analysis to be made. The method involves administering a defined amount of a labelled "metaprobe" substrate of the gateway enzyme to a subject, at a site that provides access to a desired pool of the gateway enzyme in the subject, and measuring the amount of the chosen labelled product. The presence and amount of the chosen labelled product in, e.g., the breath, definitively indicates that the labelled metaprobe has been metabolized by the specific enzyme in the specific biochemical pathway under consideration, and from the calculated rate of substrate- product conversion by the gateway enzyme, the desired diagnostic determination may be made. Likewise, if a specific therapeutic treatment for a disease is underway with a patient, this method allows for a minimally invasive assessment of the effectiveness of the treatment, with minimal discomfort to the patient.

The usefulness of the method of the invention depends on careful determination of the appropriate metaprobe substrate of the selected gateway enzyme. One aspect of such a determination can consist of structurally modifying an enzyme's natural substrate into a surrogate substrate whose metabolism can be measured in vivo in spite of confounding biochemical and physiological circumstances. Another aspect of metaprobe selection is a determination of the most appropriate location of the labelled portion so that the chosen product to be measured is labelled appropriately. Additionally, a further desirable characteristic of a metaprobe is that its enzymatic conversion product be (1) accessible by non-invasive or minimally invasive means, to allow isolation from the biological system containing it, and then be (2) amenable to rapid quantitative analysis for its isotopic content. In other words, the ideal metaprobe should permit clear and rapid differentiation between precursor and product so that calculations of rate of precursor conversion into product, and other rate-dependent parameters, are unambiguous.

In another aspect, the invention relates to labelled metaprobes, and to methods for their synthesis, for use in determination of the rate of in vivo enzyme activity, e.g., of gateway enzymes, such as disclosed herein. A particularly advantageous embodiment comprises a metaprobe having a structure comprising a release tag portion, a core tracer portion, and a derivative complex portion.

BRIEF DESCRIPTION OF THE DRAWINGS

Other features and advantages of the invention will be apparent from the following detailed description of the preferred embodiments thereof and from the claims, taken in conjunction with the accompanying drawings, in which:

FIG. 1b illustrates the superset of gateway enzymes involved in regulation of glutathione homeostasis;

FIG. 3 illustrates gateway enzymes in the homocysteine/methionine cycle;

FIG. 4 illustrates gateway enzymes in the hexosamine-insulin resistance pathway;

FIG. 5 depicts an exemplary set of metaprobes for oxoprolinase;

FIG. 7 depicts an exemplary set of metaprobes for chymotrypsin;

FIG. 8 depicts an exemplary set of metaprobes for γ-glutamyl transferase (GGT);

FIG. 10 depicts an exemplary set of metaprobes for nitric oxide synthase;

FIG. 11a depicts an exemplary set of metaprobes for cystathionine synthetase (part 1);

FIG. 11b depicts an exemplary set of metaprobes for cystathionine synthetase (part 2);

FIG. 12a depicts an exemplary set of metaprobes for glutamine fructose-6-phosphate amidotransferase (part 1)

DETAILED DESCRIPTION OF THE INVENTION

Figure 1A:
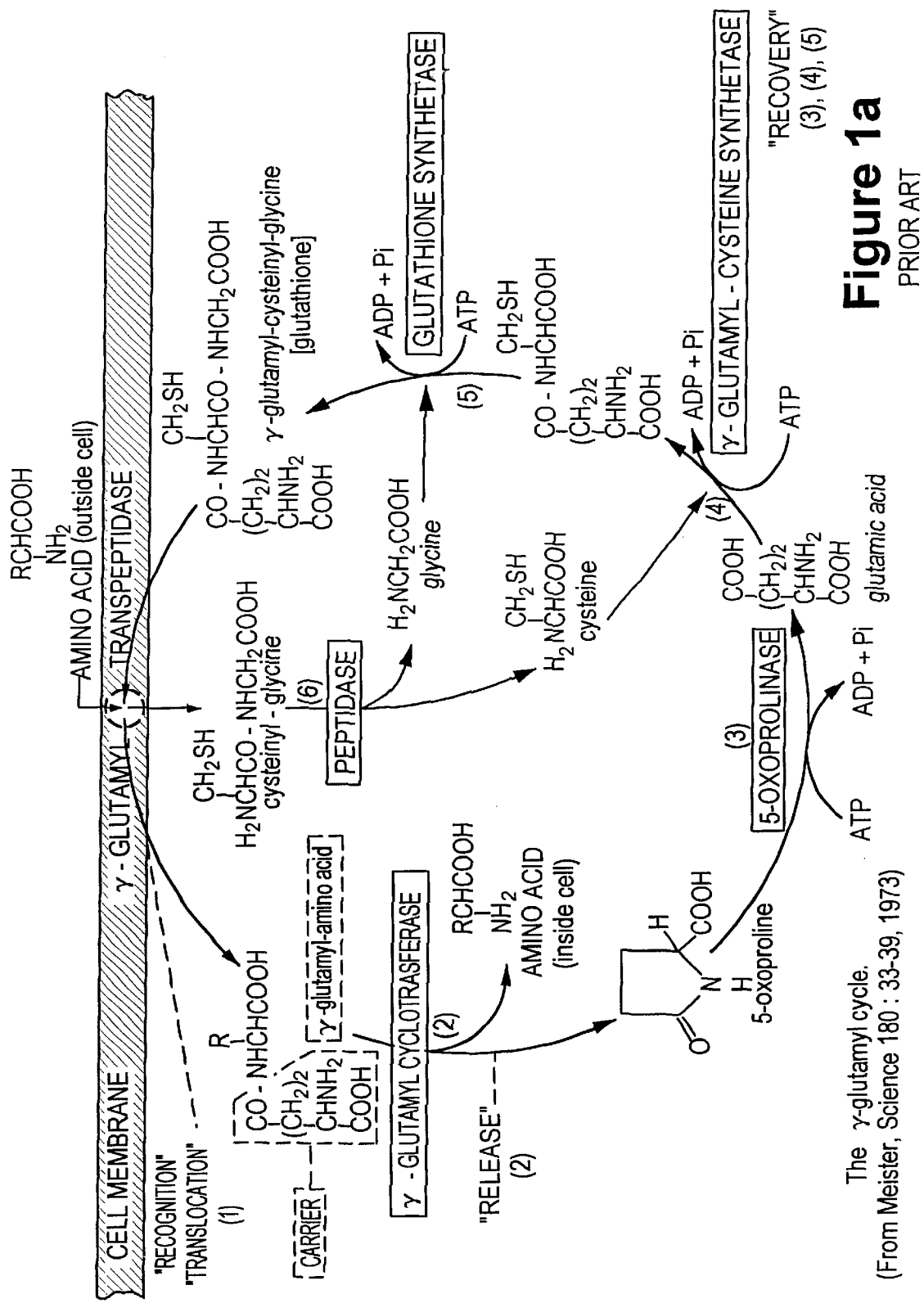
FIG. 1a illustrates gateway enzymes in the γ-glutamyl cycle of the glutathione cytoprotecting system.

The present invention relates to in vivo analytical methods for determining the rate of substrate-product conversion for gateway enzymes important to therapy management, using specially selected, labelled metaprobes, as disclosed herein. The presence or absence of labelled waste product, e.g., $^{13}CO_2$ detected in the breath, following the administration of a chosen metaprobe, can be used to definitively ascertain the presence or absence of a particular condition. The approach disclosed herein addresses the need to obtain rapid, specific and precise information about the precursor-product interconversion rates of "gateway" enzymes, either on a whole-body or organ by organ basis, in mammals and especially in human subjects.

In the living organism, gateway enzymes are components of a dynamic process comprising the biochemical economy of the host. Substrates are converted into products which, in turn, undergo additional conversions by neighboring enzymes within the same tissue structure and/or are translocated to other spatially distinct organ compartments where they are further metabolized over time. Whereas enzyme function in vitro is by its very nature isolated and episodic, the circumstance in vivo is precisely the opposite, namely, codependent and continuous. In vivo, enzymes are regenerated and their concentration subject to fluctuation. Nor are their precursor-product concentrations predictable, owing to endogenous substrate cycling, or controllable by exogenous addition or removal.

"Gateway enzymes", as used herein, refer to enzymes representing regulatory points that are 1) homeostatic (they preserve a biochemical status quo), or 2) allostatic (they permit adaptation and survival under conditions of rapid biochemical change and stress.) In terms of genetic regulation, the former tend to be constitutive enzymes, while the latter are more likely to be inducible. In either case, gateway enzymes provide functional site(s) at which the throughput of substrates and/or their metabolites can be quantitatively monitored for establishing normative values under homeostatic conditions and extreme tolerances under allostatic conditions.

For purposes of the present disclosure, gateway enzymes may be classified into one or more of the following categories:

Class I: An entry into a discrete biochemical pathway that is the starting point for a cascade of biochemical events;

Class II: A "bottleneck" or "constriction" within a discrete biochemical pathway which regulates the unidirectional and irreversible conversion of precursor substrate into product; or Class III: A "floodgate" within a biochemical pathway which is inducible in response to traumatic or catastrophic pathophysiological events.

Class I gateway enzymes generally function as mediators of absorption and transport, and are taken from the general families of membrane-bound enzymes in the walls of the digestive tract, of secretory and excretory organs, of circulatory vessels, and of cells and organelles associated with energy production or xenobiotic detoxification.

Class II gateway enzymes may be identified as the causative agents in "in-born" errors of metabolism or endocrine dysregulation. These diseases are mediated by extreme cases of bottlenecks caused by genetic deficits in the gateway enzyme's ability to function properly, with the overt result that its substrate accumulates in toxic proportions. These bottlenecks are defined functionally, for example, in terms of great disparities in the Michaelis-Menten constants ($K_m$) between the gateway enzyme and its nearest neighbors. Most pathophysiological conditions are known to emulate one or more of these metabolic aberrations. It follows that most of the gateway enzymes responsible for genetic metabolic abnormalities or endocrine dysregulation are the same ones that can be probed for aberrant function under disease conditions.

Class III gateway enzymes include those whose metabolic products become manifested during acute conditions of oxidant stress; or chemokine and lymphokine mediated acute phase responses to trauma, sepsis, or viral load; or insult by cytostatic drugs or immunosuppressive agents.

Non-limiting examples of gateway enzymes, grouped by the classes defined above, are set forth below in Tables 1, 2 and 3, including a description of their normal physiological role, and their diagnostic significance in the assessment of pathophysiological conditions. It should be noted that more than one classification may apply to any given gateway enzyme. For example, an enzyme that serves as a pathway "fentry" (i.e., Class I) under normal or homeostatic conditions may be found to respond to inductive stimuli under allostatic or pathophysiological conditions, thereby becoming a "floodgate" (Class III); and vice versa.

TABLE 1

Class I Gateway Enzymes

Arginase

Principal modulator of urea production and the turnover of ureotelic pools. This enzyme regulates the fate of arginine and the substrate availability for the synthesis of creatine and polyamines. It provides the entry point into the urea cycle and related nitrogen excretory pathways. Under pathophysiological conditions, arginase is the gateway enzyme in the catabolic cascade controlling nitrogen loss during trauma and sepsis (Class III). Arginase is also the gateway for urea production, and subsequent consumption, by intraluminal pathogenic bacteria during infection of the upper GI tract and lungs, a process that can become uncontrollable except by therapeutic intervention.

Chymotrypsin

Initiates hydrolysis of aromatic amino acid peptides in proteins; specific pancreatic enzyme so serves as an indicator of normal pancreatic function.

Cystathionine synthase

Initiates the first step in the transfer of sulfur from methionine into cysteine and is the principal non-folate dependent mechanism for clearance of homocysteine, which is known to be a causative agent in cardiovascular disease. When homocysteine remethylation becomes saturated or inhibited under pathophysiological conditions, the cystathionine synthase then functions as the bottleneck (Class II) in this detoxifying pathway. It also becomes a bottleneck in the conversion of serine to cysteine, the latter an indispensible amino acid for immune system function.

γ-Glutamyl transpeptidase

Membrane-bound transporter of glutamyl residues; mediates entry of glutathione into cells of the digestive tract. Activity becomes abnormal in cancer and immunosuppressive (Class III) and becomes limiting under conditions of septic insult (Class Initiates metabolism of xenobiotics by conjugation. Activity becomes abnormal in response to xenobiotic load, especially by cytostatic drugs (Class III) or becomes limiting under immunosuppression (Class II); serves as an indicator of antioxidant status.

Palmitoyl transferase

Membrane bound translocator of fatty acids, initiates metabolism of serine and carnitine esters in the production cascade of complex membrane lipids. Becomes a limiting gateway (Class II) in diabetes and kidney disease.

Phospholipase-A2

Initiates first steps in the cascade of phospholipid metabolism. Becomes limiting in pancreatic and neurological disorders that are consequent to changes in neuronal cell membrane repair (Class II); uncontrolled activity of the extracellular forms (Class III) becomes an allostatic factor in inflammatory disease.

Trypsin (Pancreatic)

Initiates activation of all zymogens prior to digestion. Becomes limiting (Class II) in pancreatic disease.

TABLE 2

Class II Gateway Enzymes

Alanine-glyoxylate aminotransferase

Regulates glyoxylate clearance in the liver. Limiting when liver peroxisomal enzymes become overloaded by oxidant stress.

TABLE 2-continued

Class II Gateway Enzymes

Elastase

Regulates the metabolism of elastin but also initiates metabolism of lipophilic (aliphatic amino acid rich) peptides during digestion (Class I). Becomes limiting in pancreatic disease and in neurological conditions attributable to impaired clearance of elastin in tissues and cells, such as neutrophils, in cystic fibrosis.

Glutamine-fructose-6-phosphate aminotransferase

Rate limiting enzyme in hexosamine synthesis; enzyme system capacity forecasts insulin resistance.

α-Ketoacid decarboxylase (mitochondrial)

Regulates disposal of toxic products of amino acid transaminations and participates in homeostatic mechanism for liver and kidney function. Activity varies widely under pathophysiological conditions triggered by diabetes and alcoholism and, therefore, becomes an indicator of severity and risk.

Liver N-acetyl transferase (Nati)

Limiting pathway for monomorphic substrate clearance by acetylation. Becomes suppressed under conditions of multiple drug toxicity, especially when HIV positive individual become symptomatic.

Microsomal oxidase (P450 dependent)

Regulates disposal of xenobiotics by hydroxylation. Activity is inducible in response to toxic load (Class III) but also can be suppressed by multiple drug interactions and hepatotoxic agents.

Oxoprolinase

Principal constitutive enzyme of the γ-glutamyl cycle and regulates the recycling of glutamyl residues via clearance of oxoproline. Activity becomes limiting in trauma and sepsis or during conditions of rapid glutathione synthesis. Serves as a marker for glutathione and, therefore, for cell cytoprotection capacity.

Sulfite oxidase

Limiting enzyme for the clearance of sulfur oxides that are by-products of oxidant stress in liver heart and kidney. Indicator of homeostatic capacity under normal conditions and allostatic capacity when pathophysiological conditions are suspected.

TABLE 3

Class III Gateway Enzymes

Angiotensin converting enzyme

Uncontrolled production leads to hypertension and cardiovascular disease. Activity is an indicator for efficacy of therapeutic intervention.

Human HIV protease

Mediates proliferation of HIV viral load. Becomes resistant to protease inhibitors and, therefore, can be used to gauge the efficacy and extent of therapeutic intervention.

Nitric oxide synthase

Principal modulator of free radical and NO mediated cell signaling. Triggers acute chemokine and lymphokine responses; becomes uncontrollable during trauma and sepsis, then triggers fatal multiple organ system failure; implicated in acute disorders such as preeclampsia and chronic disorders such as vascular disease.

Peroxysomal peroxidase

Principal modulator of oxygen free radical biochemistry and a principal effector of the lipid peroxydation cascade.

TABLE 3-continued

Class III Gateway Enzymes

Indicator for high risk of cardiovascular and diabetic disorders and of severity of inflammation.

Operationally, the major obstacle to the implementation of diagnostic tracer studies on gateway enzyme function is the analytical burden of quantitating the precursor product relationship. The product of the enzymatic transformation must be differentiated from the precursor, before it itself undergoes subsequent and further metabolism, or is resynthesized via common reversible pathways into another copy of the precursor molecule from which it originated. As such, an important aspect of the present disclosure relates to the "direct" determination of metabolites of the labelled substrate.

"Direct" determination is possible if the product to be detected, i.e., the product bearing the traced label, is carefully chosen. For example, the detected product metabolite must be released at the time of action of the gateway enzyme or immediately metabolized from the released products. The product must be immediately detectable externally to the patient or else the product must be stable and temporarily captured, e.g., absorbed by a body tissue where it is not further metabolized or sequestered as a stable conjugate intended for excretion, and remain capable of later detection. The preferred forms of tracer-bearing metabolic products for the purpose of direct detection are small water soluble molecules such as ammonia, bicarbonate, urea, nitrate, as well all the larger molecules that are rapidly converted into them by either biochemical processes in vivo or by microchemical manipulation ex vivo. Thus, the class of preferred metabolites also includes acetate, butyrate, formate, propionate, and related small chain aliphatic, 2-amino, guanidino, 2- or 3-hydroxy-, 2- or 3-keto-acids, methanol, ethanol and urea.

Therefore, a further aspect of the invention relates to labelled metaprobes which allow for such "direct" determination, permitting clear and rapid differentiation is between precursor and product so that calculations of rate and other rate-dependent parameters, of precursor conversion into product are based on irreversible and unidirectional enzymatic transformation. The labelled metabolites/enzymatic conversion products are accessible by non-invasive or minimally invasive means, such as breath tests, and are amenable to rapid quantitative analysis for their isotopic content.

The term "metaprobe" as used herein is meant to refer to a compound that can act as a substrate for a gateway enzyme or enzymes and that, when administered to a patient in vivo, is acted upon by that enzyme so as to produce at least one labelled "end product" that is not processed further by the subject's normally available biochemical systems. Typically, this means 1) that the labelled end product is a usual waste byproduct of the subject organism, which proceeds directly to excretion or, alternatively, finds its way to a location of the organism where it may reside until excretion, e.g., in fatty tissue or gall bladder; in sweat, tear or salivary gland; in kidney or colon; or 2) that immediately after the metaprobe is acted upon by the gateway enzyme, the labelled portion of the product is immediately converted into a (labelled) waste byproduct and is directly excreted, or, alternatively stored for a time as described above. Once the product is excreted, a "direct" determination of the gateway enzyme activity may be carried out by measuring the isotopic concentration in the waste stream, e.g., $^{13}CO_2$ in the breath, bicarbonate ions in plasma or $^{15}N$-urea in urine, so as to generate an impulse response curve.

The specific structure of the metaprobe will of course be dependent on, inter alia, an understanding of the particular gateway enzyme structure and substrate chemistry, the desired labeling isotope, and the biochemical pathway(s) of interest. An ideal metaprobe will consist of three components, although any two may be combined into a single, but bifunctional molecular entity: 1) a release tag; 2) a core tracer component or moiety; and 3) a derivative complex component or moiety. The "release tag" as a component of the metaprobe is the unique identifier. The "core tracer" constituent of the metaprobe is that portion of the molecule that is acted upon to trace the biochemical process under investigation. The derivative complex is the chemical "packaging" or structural "cloaking" that permits the core tracer to withstand its journey through incidental biochemical pathways on route to its point of delivery, the desired gateway enzyme.

The release tag component of a metaprobe may include the following: 1) A functional group labelled with a stable (non-radioactive) nuclide of, preferably, carbon, hydrogen, nitrogen, oxygen, or sulfur; however, any other radioactive or stable nuclide whose abundance in living organisms is approximately 5% or less by weight of elemental composition may be used. 2) A functional group selected from the group consisting of $C_1$ to $C_3$ moieties of molecular weight less than 100 Daltons that are $^{13}C$ or other isotopic carbon-labelled derivatives of carboxylic acid, aldehyde, nitrile, aldimine, formamido, acetamido, propionamido, methoxy, ethoxy, propoxy, formyloxy, acetoxy, propionoxy, acetamidino, and formamidino, guanido, guanidino, and ureido functional groups that a) when oxidized enzymatically, result in labelled isotopic carbon-containing carbon monoxide, carbon dioxide, formic acid, acetic acid, acetone, acetaldehyde, propionaldehyde, propionic acid, cyanide, formamide, acetamide, or urea; or b) when chemically oxidized, thermolytically or thermochemolytically treated, result in labelled carbon monoxide, carbon dioxide, methane, ethane, propane, acetone, acetaldehyde, propionaldehyde, cyanide radicals, hydrogen cyanide, cyanate radicals, hydrogen cyanate, formic acid, acetic acid, propionic acid, formamide, or cyanamide. 3) A functional group selected from the group consisting of $C_1$ to $C_3$ moieties of molecular weight less than 100 Daltons that are $^{15}N$ or other isotopic nitrogen-labelled derivatives of nitrile, aldimine, formamido, acetamido, acetamidino, and formamidino, guanido, guanidino, and ureido functional groups that a) when oxidized enzymatically, result in isotopic nitrogen-containing nitrogen gas, nitric oxide, nitrite anion, nitrate anion, ammonia, cyanide, formamide, acetamide, or urea; or b) when chemically oxidized, thermolytically or thermochemolytically treated, result in labelled nitrogen gas, nitric oxide, nitrous oxide, cyanide radicals, hydrogen cyanide, cyanate radicals, hydrogen cyanate, formamide, formamidine, or cyanamide. 4) A functional group selected from the group consisting of $C_1$ to $C_3$ moieties of molecular weight less than 100 Daltons that are $^{18}O$ or other isotopic oxygen-labelled derivatives of carboxylic acid, aldehyde, formamido, acetamido, methoxy, ethoxy, formyloxy, acetoxy, formamidino, guanido, and ureido functional groups that a) when oxidized enzymatically, result in isotopic-labelled oxygen-containing carbon monoxide, carbon dioxide, formic acid, acetic acid, propionic acid, acetone, acetaldehyde, propionaldehyde, formamide, acetamide, or urea; or b) when chemically oxidized, thermolytically or thermochemolytically treated, result in labelled carbon monoxide, carbon dioxide, cyanate radicals, hydrogen cyanate, formic acid, acetic acid, propionic acid, or formamide. 5) A functional group selected from the group consisting of $C_1$ to $C_3$ moieties of molecular weight less than 100 Daltons that are $^{34}S$ or other isotopic sulfur-labelled sulfur analogs of the carbonyl, hydroxy or other oxygen functionality-containing functional groups listed above.

consisting of 2-amino-aliphatic acids. In the case of core tracers whose pendant release tags are intended for removal by non-enzymatic means, the preferred embodiments consist of a) molecules that are not natural biosynthetic products of mammals or b) molecules that are not metabolized by mammals or c) those 2-amino-aliphatic acids that are not found in mammalian proteins, although they may be biosynthesized and metabolized. The preferred modifiable groups are shown in Table 4, below.

TABLE IV

REVERSIBLE PROTECTING GROUPS

| Modifiable Group | $R^a$ | Reversible Group | $Z^a$ |
|---|---|---|---|
| RC=O | H, Ak, A | $RC(OZ)_2$ | Ak |
| | H | $HC(O_2CZ)_2$ | Ak, Ar |
| | H, Ak, Ar | C=C—OZ | Ak |
| | H, Ak, Ar | C=C—$NZ^1Z^2$ | Ak |
| | H | $CHCl(O_2CZ)$ | Ak, Ar |
| | H, Ak, Ar | C=NZ | Ak, Ar, OMe |
| | H, Ak, Ar | [thiazolidine structure] | H, $CO_2Ak$ |
| | H, Ak, Ar | C=C—$O_2CZ$ | Ak, Ar |
| $CO_2H$ | — | $CO_2Z$ | Ak, Ar |
| | — | C=O(SZ) | Ak, Ar |
| | — | C=O($NZ^1Z^2$) | H, Ak, Ar, OH, $NH_2$ |
| | — | $CO_2CHZ^1O_2CZ^2$ | $Z^1$ = H, Ph; $Z^2$ = Ak, Ar |
| | — | $CO_2CHZCl$ | H, Ar |
| | — | $C(OZ)_3$ | Ak |
| | — | $CO_2CO_2Z$ | Ak, Ar |
| | — | $CO_2CH_2Z$ | SMe, SOMe, $SO_2Me$ |
| CONHR | H | $CONHCH_2NZ^1Z^2$ | Ak, Ar |
| | H | $CONHCH_2OH$ | — |
| OH | — | $O_2CZ$ | Ak, Ar, . . . |
| | — | $(—O_3)CZ$ | Ak, Ar, . . . |
| | — | OZ | Ak, Ar |
| | — | —O—C=C | — |
| | — | $(—O—)_2CZ^1Z^2$ | H, Ak, Ar |
| | — | $O_2CNZ^1Z^2$ | H, Ak, Ar |
| | — | $O_2COZ$ | H, Ak, Ar |
| | — | $O_2CO_2Z$ | H, Ak, Ar |
| | — | $OSiZ_3$ | Ak |
| | — | $(—O)_2CO$ | — |
| | — | $(—O)_3PO$ | — |
| | — | $(—O)_2SO_2$ | — |
| NHR | H, Ak, Ar | NR(C=O)Z | Ak, Ar |
| | H, Ak, Ar | $NRCO_2Z$ | Ak, Ar |
| | H, Ak, Ar | NRC=C | — |
| | H, Ak, Ar | NR(C=O)NHZ | Ak, Ar |
| | Ar | [succinimide-CH2-NAr structure] | — |
| RN(R)H | H, Ak, Ar | $RN(R)CH_2O_2CZ$ | Ak, Ar |
| SH | — | S(C=O)Z | Ak, Ar |

$^a$Ak, Alkyl; Ar, aryl; adapted from Charton, M. Methods in Enzymology, 112, p. 331 (Table I), 1985

The core tracer may be defined as a functionalized $C_2$ or greater alkyl or aralkyl hydrocarbon moieties having one or more modifiable groups, at least one of which comprises the release tag as a discrete substituent at either a terminus of the moiety (as opposed to embedded within the backbone of the chain or ring) or at both ends, the preferred embodiments The derivative complex may be characterized as one or more reversible derivative groups, also taken from the list in Table 4, which may be attached to the tracer core either at the site of the release tag, or elsewhere along the carbon skeleton of the core. The purpose of the derivative complex is to impart the necessary steric, affinity and other physicochemical properties to permit the entire metaprobe to function as a substrate for the intended gateway enzyme. The derivative complex also serves to modulate the solubility, lipophilicity, partition coefficient, and diffusional properties of the metaprobe so as to facilitate transport and delivery to the site of metabolism. The derivative complex desirably includes a) those groups that are resistant to uncatalyzed aqueous solvolysis under physiological conditions but b) are rapidly hydrolyzed by non-specific esterases and peptidases found in biological fluids and c) that impart to the metaprobe a partition coefficient, such as the octanol/water Logp value, in the range of +1 to +4 and falling within +25% of the corresponding values for any of the natural substrates known to be metabolized by the gateway enzyme.

A final preferred embodiment of the metaprobe design are those combinations of release tag, core tracer and derivative complex that taken as a whole permit the metaprobe to be metabolized by its gateway enzyme in measurable amounts within 2 hours of its introduction into the host organism under study. More detailed teachings as to metaprobe design criteria can be summarized in terms of several rubrics that, if followed, will yield metaprobes of demonstrable utility. The design of any metaprobe must be biologically sound and concordant with the biochemical and physico-chemical relationships of the biological system that they are targeted towards. In practical, terms, as to biological properties, the tracer core and carrier complex moieties of a metaprobe must be sufficiently soluble in biological fluids so as to be transported either by passive diffusion or by facilitated biophysical processes. Their molecular structures, therefore, should not include functional groups that can be predicted to facilitate crystallization, flocculation or polymerization in the lumen of the digestive tract or within the circulatory, respiratory or genitourinary systems.

The entire metaprobe, and each of its component parts should display no detectable activity when assayed as a biological reponse modifier, hormone, toxicant or xenobiotic, or acute toxicity in standard toxicological safety assays, either in vivo or in surrogate systems, should fall above doses in excess of 2000 mg/kg. Nor should metaprobes incorporate any components contributing to detectable pyrogenicity or endotoxin reactivity. Therefore, metaprobes should be constructed with chemical likages and functionalities that render the molecule amenable to sterilization when in solution, eiher by heat (autoclaving), irradiation or ultrafiltration. Furthermore, metaprobes should be both compatible with and non-reactive toward common food additives, excipients and inert ingredients that are generally found in over-the-counter pharmaceuticals, cosmetics and other formulated personal care products that are designed for ingestion or topical application.

In terms of their extended chemical properties, the molecular relationships between and among release tag, core tracer and carrier complex must be harmonized so that the properties of one do not interfere with the proper function of the others. For example, in the selection process for enzymatically hydrolyzeable release tags, such as carbonyl, formyl, acetyl, propionyl, or for heteroalkyl release tags amenable to oxidative removal, such as O-, N-, S-methylated or ethylated species, the metaprobe designer must chose all other substituents within the core tracer, including those required to form the derivative complex, in such a way as to minimize the steric and electronic effects which might inhibit the rapid removal of the release tag.

The selection of substituents and the configuration of linkages between component parts of a metaprobe, whose analysis is dependent on release tag removal by non-enzymatic means (e.g., thermolysis, pyrolysis, photoactivation, catalytic cleavage, destructive oxidation or chemical sequestration) should be tailored so that the fractional rate of release tag removal and its isotopic enrichment are not compromised. In other words, in the course of optimizing metaprobe design, it is necessary to model the structural properties of the core tracer-release tag-carrier complex combined motif so that the introduction of substituents onto any given part of a metaprobe do not militate, by means of steric or electronic interactions, against the affinity of the metaprobe towards the gateway enzyme domain that it is intended to probe. Further, the design of the metaprobe's constituent parts should not impair the reactivity of the release tag towards enzymatic or physico-chemical removal.

Both these classes of metaprobe design optimization requirements can be addressed by skilled practitioners of organic chemical discovery through the use of QSAR and related forms of a priori molecular property analysis. Procedures for doing so are readily available within the corpus of traditional methods for chemical discovery (Topliss, 1983) or in the contemporary context of combinatorial chemistry design and chemical informatics. Chemical property prediction software is readily available commercially, as exemplified by I-LAB and QSPR (Acdlabs, Inc.) and the PALLAS modules (Compudrug, Inc.). These software packages may be used as standalone applications for metaprobe design and can also be augmented by incorporating published rubrics for functional group and "prodrug" lability (Charton, 1985; Hansch, 1972). These expert systems can afford the requisite and indispensible design information about any proposed metaprobe with respect to its putative acidity/basicity, partition coefficient, distribution coefficient, metabolic inactivation, chemical lability, toxicity, stereochemistry and reactivity. By comparing and contrasting these types of physical characteristics with those of known gateway enzyme substrates, the construction of analogous metaprobes can be modulated so as to optimize their biological function and affinity to the target gateway enzyme.

An alternate approach in guiding the metaprobe design process would be to test its properties back to back with those of known substrates for the gateway enzyme. In vitro bioassays can be developed so as to determine the relative metabolic rates of tracer labelled substrates. Many of these have been published in the *Methods in Ezymology* (New York, Academic Press) and related monographic series, especially as microdose assays for evaluating the kinetics of hydrolytic or oxidative processes (Bircher and Preisig, 1981; Davidson et sl., 1981; Griffith, 1985; Vann et al., 1977). Thus, any metaprobe can be assessed in vitro for the efficiency of its design prior to further application in vivo. Taken as a whole, these aforementioned methodological steps have been those invoked in arriving at the preferred subset of metaprobes described in subsequent illustrative examples.

From the general discussion of metaprobe design, it can be seen that all candidate molecules share in common certain structural properties that render them useful as diagnostic probes for the underlying enzymatic pathways whose function they are designed to probe. In qualitative terms, metaprobes are substrates for their respective gateways. Thus, in addition to the chemical properties for the combination of release tag, core tracer and derivative complex, the metaprobes described in this invention may share as a common characteristic the fact that they are analogs of known therapeutic agents, when these latter themselves are known inhibitors of the gateway enzymes that are the target of their therapeutic mode of action.

When applicable, a preferred embodiment of the metaprobe concept consists of isotopically labelled analogs of therapeutic drugs that retain the isosteric and electronic properties of that drug but do not show any potency as biological effectors because the non-scissile bonds of the therapeutic congener have been replaced with hydrolyzable ones. Therapeutic agents that inhibit gateway enzymes are designed specifically for their resistance to enzymatic conversion. In contrast, their analogous metaprobes, when acting as substrates in the context of this invention, must consist of molecular configurations that permit them to become rapidly metabolized. Consequently, in this invention, a preponderance of favored metaprobes are assembled from constituent parts taken from the amino acid family of molecules, and especially those amino acids that are not incorporated into the protein synthesis pool. Molecules of this kind are generally regarded as safe, do not have drug potency, and can be readily assembled via peptide bonds, or other amide and ester linkages, into molecules whose design adheres both to the physiochemical and structural properties specified by the definition of suitable metaprobes in accordance with this invention.

The examples that follow illustrate how the basic structure of a representative selection of metaprobes ultimately defines the structure of the analyte that is to be quantitated in order to judge the extent and efficacy of the gateway enzyme acting upon it. They are intended to identify the basic structure and acceptable structural variations of metaprobes according to their mode of action at the gateway enzyme. These metaprobes are intended for use by one or more of the routes of administration, as described in the following section. It should be also understood that the fate of the component tracer core and of the release tag in each of these metaprobes may be traced and quantitated by one or more of the general methods that are customarily employed for the measurement of isotopic labels in various biological matrices, most notably by mass spectral methods applied directly to the release tag or to the tracer core. A variety of analytical techniques can be brought to bear on the detection of the isotopic content, and therefore, the rate of change in isotopic content as a function of biological residence time.

The following examples are presented to illustrate the advantages of the present invention and to assist one of ordinary skill in making and using the same. These examples are not intended in any way otherwise to limit the scope of the disclosure.

EXAMPLE I

The Method of the Invention in Generic Form

Operationally, the application of the metaprobes in this invention follows the same basic sequence of steps. The metaprobe is first tested in one or more healthy individuals in order to determine a metabolic index value for the gateway enzyme system under consideration. This is accomplished by dispensing a known dose of the metaprobe by an appropriate route of administration, which in separate instances may be either oral, intravenous, intra-arterial, intraluminal (rectal, vaginal, nasal, tracheal, otic), intrathecal, intramuscular, subcutaneous or transdermal. The preferred route of administration for analysis of gateway enzyme kinetics is oral, but for purposes of evaluating gateway enzyme metabolism beyond the splanchnic bed, it would be appropriate to dispense the metaprobe into those body compartments that are most proximate to the organ systems whose biochemical funtions are being probed.

Next, the appearance of release tag at one or more time intervals after metaprobe administration is monitored, the investigator having first taken a "blank" or background sample at the time of dosing. The preferred sampling site for analysis of gateway enzyme kinetics is in breath, which constitutes the least invasive approach, but it also may be appropriate to determine the amount of release tag in other accessible sites, such as plasma, urine, feces, luminal lavage fluids, tears, saliva, bile, sweat, or tissue samples obtained by needle aspiration or surgical biopsy. The selection of sampling site is made on the basis of how proximate it is to the tissues and organs whose gateway enzymes are under scrutiny and the extent to which organ localization is an important determinant in formulating a clinical judgement about the overall function of gateway enzymes under normal, in contrast to pathophysiological, conditions. Consideration should also be given in the selection of a sampling site to the extent that the sampling site reflects an adequate rate of appearance of release tag which, for practical purposes concerning patient comfort, should be maximal within two hours of metaprobe administration.

Finally, a metabolic index that reflects gateway enzyme activity in terms of either metaprobe rate of disappearance, release tag rate of appearance, or other kinetic measures of substrate flow through the gateway enzyme at the organ sites where metaprobe metabolism is preponderant, is calculated. Laboratory and computational procedures for carrying out such calculations have been extensively described in the academic and patent literature (Barshop et al., 1991; Bier, 1997; Browne, 1997; Cobelli et al., 1987, 1992; El-Khoury et al., 1996; Klein and Klein, 1979; Patterson, 1997; Wiechert and DeGraaf, 1996; Wolfe, 1992; and U.S. Pat. Nos. 4,676,974; 5,100,779; 5,233,997; 5,338,686; 5,386,832; 5,413,917; 5,432,058; 5,466,434; 5,628,328; 5,756,067). The standard techniques for interpreting the kinetics of tracer metabolism may also be augmented by the kinds of computational short cuts well known to pharmacokineticists, who have developed numerous methods to characterize the temporal properties of interindividual drug metabolism. In the context of metaprobe utilization, the preferred techniques are those non- compartmental and minimal compartmental (up to 4 compartments) generic models that permit deconvolution of the tracer mass balance relationships and fractional flux rates during the various phases of metaprobe absorption, core tracer distribution, and release tag irreversible disposal, regardless of route of administration (Barrett et al., 1998; Bourne, 1995; Heinzel et al., 1993; Katz, 1989; Lassen and Perl, 1979; Wagner 1976; Wagner, 1993).

The metaprobe is tested on a patient who is being evaluated for a condition in which the gateway enzyme under consideration is an indicator for pathophysiological dysregulation, using the same protocol developed on a normative cohort of healthy individuals. A suitable metabolic index based on the temporal properties of the metaprobe disposal is then computed by the same pharmacokinetic manipulations as applied to results from normal controls.

Comparison is then made between the metabolic index value obtained for the patient and the normative values for the control population. Any significant variation thereof, i.e., the metaprobe test score, is taken as a measure of disease severity and can then be tracked longitudinally as an indicator both of disease progression or remission in response to therapeutic intervention. The magnitude of the metaprobe test score may also be utilized as a management tool in the selection of gradations in therapy, or alternate therapies altogether, that are considered optional in proportion to the degree of divergence between the patient's test score and normal values or in step with the variation among individual patient test scores taken without reference to any other benchmarks. The magnitude of the metaprobe test score also can be interpreted as a measure of risk, in cases where overt symptoms of disease are not presented, and, therefore, can serve a guideline for initiation of appropriate preventive measures. In this latter implementation, the metaprobe test score serves as a prognostic or patient stratification index, pointing to the relative immediacy or future eligibility for treatment.

Further disease and therapy management information about the patient can also be obtained by administering the metaprobe test sequentially at the start of a multi-part treatment regimen. Under this operating condition, the first test score serves as the basal control value prior to initiation of the desired first intervention and any subsequent test score, taken at periodic intervals, can be used to assess whether or not the patient has returned to basal values prior to repetition of the intervention with greater frequency or intensity. In this instance, the patient serves as his/her own control. Similarly, the metaprobe test can be used as part of a stimulatory or suppression protocol aimed at determining the functional capacity or functional reserve of a target gateway enzyme. In such a protocol, the patient is tested under basal conditions and then submitted to a calculated stress or insult, either mechanical (e.g., exercise) or pharmacological in nature, intended to challenge those homeostatic mechanisms in which the gateway enzyme under evaluation is a primary effector. A second metaprobe test is performed upon completion of the challenge period, and the difference between the post and pre test scores are computed. The magnitude of any difference can be used as a metric norm for adaptive capacity and, therefore, can serve as a quantifying index among classes of patients presenting with varying degrees of disease severity or between patients and those individuals who are deemed to be healthy, normal controls.

EXAMPLE II

Enzymatic Pathways Containing Gateway Enzymes and Their Associated Disease States Gateway enzymes are essential components of three fundamental enzyme-enabled pathways that relate to the glutathione cycle and mechanisms of cytoprotection (FIGS. 1a and 1b); the arginine/nitric oxide signaling pathway (FIG. 2); the homocysteine/methionine cycle (FIG. 3); and the hexosamine/insulin resistance pathway (FIG. 4). Assessment of the glutathione cycle measures the body's ability to "bounce-back" from trauma or other insult and probably has the broadest clinical application. The measurement of cytoprotective capacity and resistance to oxidative stress, as reflected in the glutathione cycle, is immediately applicable in cancer treatment to assess a given patient's ability to withstand a dose of chemotherapy. Cancer cachexia, or wasting, also can be managed with more effective nutritional intervention, since the glutathione cycle is responsive to available nutritional supplements. Patients with AIDS, hepatitis, and long term neurodegenerative disorders, such as Parkinson's and Alzheimer's disease, might also benefit.

In combination with monitoring the glutathione cycle, assessment of the arginine/nitric oxide (NO) signaling pathway may be useful in managing ICU patients with burns, trauma, heart failure, septic shock and ARDS. Monitoring of the arginine/NO pathway may furthermore be useful to predict and manage patients with potential irreversible, runaway processes and chronic problems such as congestive heart failure, emphysema, and cachexia.

Homocysteine and related methionine derivatives are recognized markers for risk of atherosclerosis. Specifically, elevated plasma homocysteine concentrations are associated with increased risk for premature occlusive vascular diseases. Since plasma homocysteine can be managed with nutritional therapies, the method of the invention can be used to identify at risk patients, track therapy management, and lower the incidence of heart disease.

Hyperglycemia and its concomitant "glucose toxicity" effect at the cellular level has been convincingly demonstrated as the cause of most, if not all, of the chronic complications of diabetes, especially cardiovascular morbidity and mortality. The abnormal concentration of glucose in cells, once glucose homeostasis has been disrupted under pathophysiological conditions, has been linked to an increase in hexosamine flux and, therefore, to a dysregulation of the glutamine-fructose-6-phosphate aminotransferase gateway enzyme system, which then overproduces glucosamine. Excess glucosamine then causes insulin resistance, via one or more cell signaling pathways that are tuned to increased glucosamine-mediated protein glycation, and accelerates a vicious cycle that worsens the diabetic state and makes therapeutic glycemic regulation more difficult. Thus, monitoring the activity of glucosamine production by the application of a metaprobe by the method of this invention can be used to first assess the potential severity of glucose toxicity prior to the onset of its symptoms and then to track the course of its amelioration by intervention with insulin, anti-diabetic drugs or other therapeutic modalities aimed at restoring normal euglycemia.

In terms of the gateway enzymes, identified for illustrative purposes in this Example II, the diseases associated with them and enumerated at the outset of this Example can all be monitored by their biochemical signatures as embodied in metaprobe test scores. All such text scores can be elaborated in accordance with the generic protocol just described in Example I, which should be taken as the modus operandi in all subsequent illustrations of this invention.

EXAMPLE III

Use of the Method of the Invention with Oxoprolinase

Oxoprolinase is a ATP dependent enzyme in the γ-glutamyl cycle (FIG. 1a) with the lowest Km in the sequence (Jackson et al., 1996; Meister et al., 1985; Meister, 1989). As such, it represents a bottleneck whose activity can therefore be viewed as an indicator of overall flux through the cycle that ultimately produces glutathione, the principal antioxidant and effector of cell cytoprotection against oxidant stress. Under basal conditions of homeostasis in healthy young mammals, especially humans, the production capacity of the glutamyl cycle is held in check by a feedback mechanism preventing glutathione overproduction unless it is needed to address an insult caused exogenously by trauma, bacterial or viral insult, or endogenously by cytokine/chemokyne cell signaling cascades that are triggered by pathophysiological conditions in organs of the splanchnic bed or of the cardiovascular system.

Thus, under normal conditions, precursors from the glutamyl transpeptidase and the glutamyl cyclotransferase are shunted into oxoprolinase as its natural substrate oxoproline. In fact, when glutathione synthesis is inhibited chemically or blocked genetically in inborn errors of metabolism, oxoproline will accumulate in toxic concentrations because the oxoprolinase kinetic bottleneck cannot metabolize the overload. Conversely, during periods of high glutathione demand, in order to meet the needs for increased cell cytoprotection and xenobiotic detoxification, the substrate flow is shunted towards the production of glutamylcysteine, leaving little material for conversion by the cyclotransferase into oxoproline and its subsequent hydrolysis to glutamate by the oxoprolinase bottleneck.

Ideal metaprobes for the oxoprolinase gateway, and, therefore, indicators of the overall throughput of substrate through the γ-glutamyl cycle, include tracer labelled variants of oxoproline and its structural analogs, whose physicochemical properties are compatible motifs, in accordance with the rules for metaprobe design, with the oxoprolinase active site domain. These include, as shown in FIG. 5, analogs and homologs of oxoproline, serving as the core tracer, with a common release tag, a carbonyl group labelled preferably with $^{13}C$, that effects ring closure between the α-amino acid substituent and the thiol terminus in order to complete the carrier complex. Further structural modifications of the carrier complex, aimed at affecting lipophilicity and rate of transport from different sites of metaprobe administration, are effected by substitution of the free carboxylic acid with hydrolyzable groups, including but not limited to those shown in Table 4. But all must contain the 2-oxo-thiazolidine functionality in order to be hydrolyzed at rates within the same order of magnitude as the natural substrate, oxoproline. Accordingly, the structures shown in FIG. 5 are compliant with the requirements for competitive activity as substrates for oxoprolinase and conform to the design considerations previously enumerated in the biochemical literature about this enzyme (Meister, 1989). The utility of one such metaprobe was verfied in the following trial on human subjects.

L-2-oxo[$^{13}C$]thiazolidine-4-carboxylic acid (OTC) is a 5-oxoproline analog which when acted upon by 5-oxoprolinase, is converted to cysteine (CYS), the rate limiting amino acid for glutathione (GSH) synthesis, with the release of $CO_2$. Studies have shown that OTC administration can replete cellular GSH stores when the GSH pool has been depleted due to detoxification of drug metabolites (Giorgi et al., 1992; Kalayjian et al., 1994; Levy et al., 1998; Vita et al., 1998). In this example, it was first determined that orally administered $^{13}C$-labelled OTC could be used to detect changes in the body's GSH stores. OTC satisfies the criteria of a metaprobe to be used in the method of the invention as follows: it is a substrate of oxoprolinase and a demonstrated competitive inhibitor of oxoproline hydrolysis by enzymatic assay in vitro (Meister et al., 1985), while its pharmacokinetics of in vivo disposition are known to follow the same temporal properties of comparable doses of oxoproline; its physical properties, solubility, acidity and lipophilicity are indistinguishable from those of oxoproline; the hydrolysis of OTC instantly liberates 13$CO_2$, an ideal release tag which is rapidly transported into the peripheral circulation and exhaled into breath, and the remainder of the molecule is no longer recyclable as a substrate, that is, its hydrolysis represents a one way metabolic "street"; both the tracer core and the release tag, namely, cysteine and carbon dioxide, are natural biochemicals generally regarded as safe; and the toxicological properties of the OTC metaprobe are both demonstrably unremarkable (White et al., 1992) and less toxic than those of oxoproline itself, a natural material and constituent of the body.

Seven healthy volunteers (ages 22–39) each participated in two studies. After three days on a weight maintaining diet, each participant was given a drink containing $^{13}C$-labelled OTC (1.5 mg/kg), following which blood and expired breath were sampled frequently. In the first test, each participant received the OTC alone. In the second study at least one week later, each participant ingested 2 gm acetaminophen one hour prior to the OTC drink. Expired breath samples were analyzed for the $^{13}C$ enrichment (APE) of $CO_2$, and expressed as isotopic enrichment in atom per cent excess (APE×1000) versus time, in the usual manner and in accordance with the general protocol described in Example I. A second panel of probands (ages 53–73) were tested in a similar manner.

Figure 6:
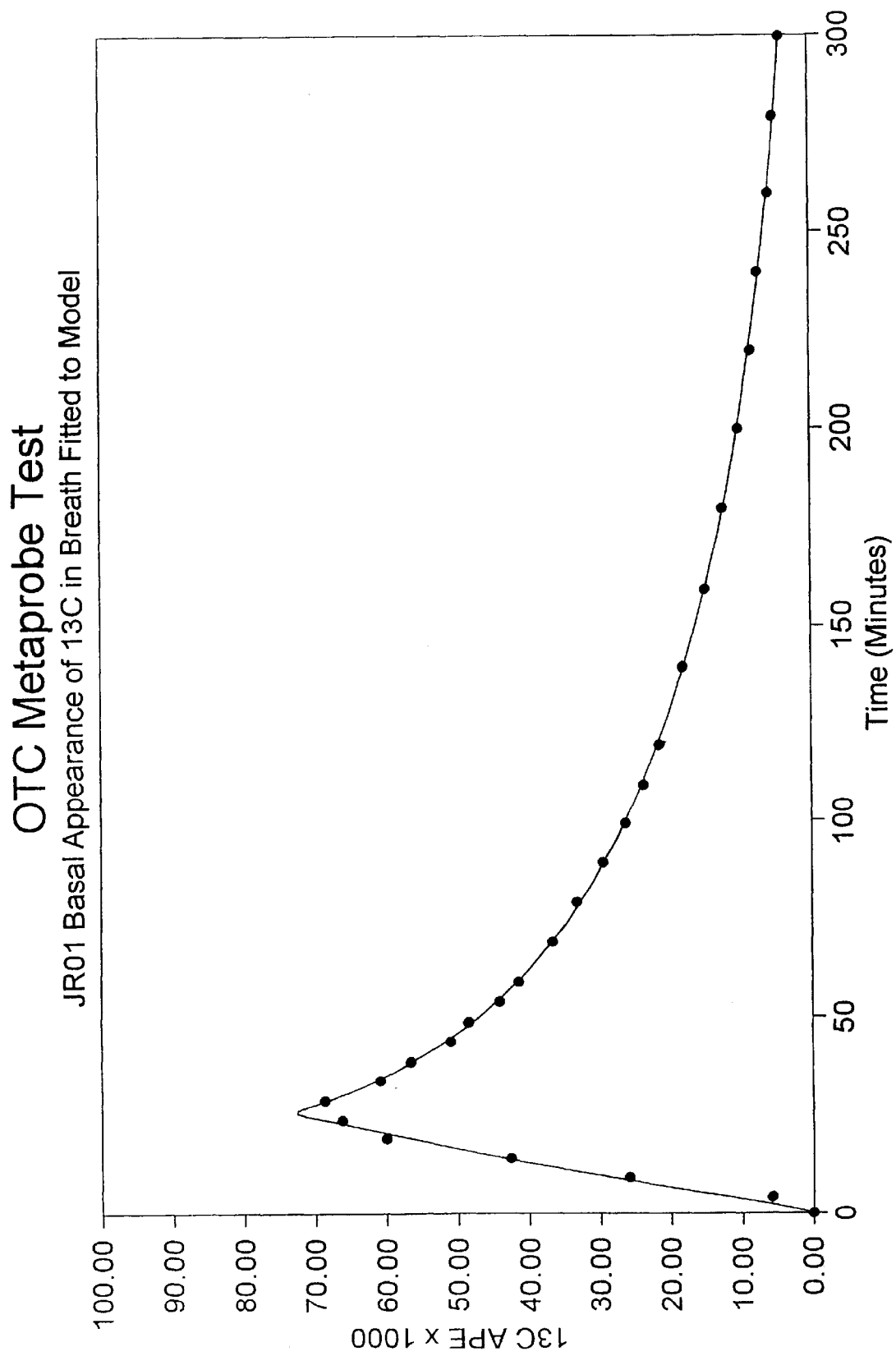
FIG. 6 depicts the kinetics of appearance of $^{13}C$—$Co_2$ release tag in breath after oral administration on an oxoprolinase metaprobe.

A representative plot showing the appearance of $^{13}C$-release tag in breath is shown in FIG. 6. From the pattern of label enrichment, at least two types of kinetic processes are apparent, one is absorption, since the metaprobe was dispensed orally, and the other disposition. Pharmacokinetic analysis of the entire "exhalation" curve, using an automated modeling program, showed that the metabolic process of OTC hydrolysis in vivo is best described, on the basis of goodness of fit criteria, as a two compartment model with lagged, zero order absorption into the peripheral plasma compartment, equilibration with a systemic metabolic compartment at the tissue level, and elimination from the peripheral compartment ultimately via the pulmonary circulation and into breath.

Deconvolution of this model by equation transformation and coefficient matching (Wagner, 1993) afforded separate kinetic measurements for the post absorptive metabolism of OTC in the metabolic compartment, and this was expressed as a fractional catabolic rate (Lassen and Perl, 1979). Lastly, the per cent of metaprobe dose recovered in breath was computed from the cumulative integral of the 13$CO_2$ enrichment versus time plot multiplied by the $CO_2$ production rate for each proband, which in these experiments were measured by indirect calorimetry (but can also be estimated from formulas that have been proven to correlate an individual's height, weight, age and gender with $CO_2$ production). The metabolic index for OTC utilization by oxoprolinase was then computed by the simple expedient of multiplying the dose of metaprobe by the per cent recovery and then by the fractional catabolic rate.

Under basal conditions when the "emergency" demand for glutathione is low, one would expect a relative surplus of incidental substrates within the T-glutamyl cycle. Conversely, under conditions of high glutathione demand and concomitant continual synthesis, such as in response to a hepatotoxic challenge from acetaminophen ingestion, one would expect proportionately lower levels of incidental substrates, such as oxoproline, because all available precursors for the glutamyl skeleton of glutathione are being shunted into glutathione production. Thus, when an oxoprolinase metaprobe is dispensed under basal conditions, there would be sufficient natural substrate, in this case oxoproline, present at the site of metabolism to compete with it. More oxoproline relative to OTC would be expected to be metabolized per unit time, resulting in a lower relative rate of OTC conversion and a lower cumulative level of release tag appearance at the sampling site in breath. By contrast, in response to a glutathione depleting stimulus, glutathione production becomes elevated, oxoproline synthesis is suppressed for lack of glutamyl substrates, and therefore the oxoprolinase gateway enzyme can metabolize exogenously added metaprobe at a faster relative rate, resulting in the appearance of higher amounts of release tag in breath than under basal conditions.

The data from the validating trial in this Example III all corroborate the biochemical hypothesis concerning the OTC metaprobe's mode of action as an indicator of oxoprolinase activity and, therefore, its utility as a surrogate indicator for glutathione production capacity. The results, which are expressed in terms of nanomoles of OTC metabolized per kilogram body weight per minute for the basal condition (BASAL), post acetaminophen (ACE+), and the stimulatory difference between ACE+ and BASAL (STIM) are shown in Table 5.

TABLE 5

Metabolic Rate Index (nMol/kG/min) After an Oral Dose of $^{13}$C-OTC With and Without Acetaminophen

| AGE | YOUNG (22–39 yrs., n = 7) | OLD (53–73 yrs., n = 5) | ALL (22–73 yrs., n = 12) |
|---|---|---|---|
| BASAL | 286 +/− 111 | 335 +/− 110 | 307 +/− 108 |
| ACE+ | 547 +/− 269 | 452 +/− 161 | 515 +/− 227 |
| STIM | 261 +/− 115 | 117 +/− 40 | 208 +/− 82 |

In all subjects, the metabolic rate index of the OTC metaprobe was significantly higher (p<.05) after the glutathione depleting insult than before. The YOUNG set showed a lower basal level and a higher level of metaprobe utilization, consistent with the view that glutathione homeostasis is altered by the aging process and, therefore, a more prolonged exposure to oxidant stress. The difference in adaptive capacity, as measured by the STIM parameter, was twice as large in the YOUNG than in the OLD and was highly significant (p<.01). Taken as a whole, these data support the hypothesis that the OTC metaprobe effectively tracks the course of glutathione depletion, even after a mild insult, and can also be used to estimate the relative capacity of the glutathione production machinery in cohorts with different oxidant stress histories.

By extending the application of the OTC metaprobe to therapy management, it should be possible, in a similar manner, to stratify probands both according to their basal OTC metabolic index and to their production capacity in response to a controlled insult, such as that provided by acetaminophen. Patients with a high basal metabolic index and/or a low STIM score would be the least likely to benefit from antioxidant and related therapies aimed at boosting the glutathione machinery, e.g., in AIDS (Kalayjian et al., 1994) and cardiovascular disease (Vita et al., 1998) and can be predicted to be the most susceptible to harm from treatments, such as chemotherapy, whose coincident biochemical effects include chronic GSH depletion, e.g., hemorrhagic cystitis (White, et al. 1995) and bone marrow hypoplasia (Goldberg et al., 1995). By extension, the estimation of an OTC metaprobe STIM value in patients contemplating any intervention that might be expected to weaken glutathione mediated host defenses can be expected to foreshadow their relative ability to maintain glutathione homeostasis. Patients with higher BASAL scores and lower STIM scores would predictably be the ones to sustain higher morbidity and mortality.

EXAMPLE IV

Use of the Method of the Invention with Chymotrypsin

The pancreatic enzyme chymotrypsin attacks substrates containing the aromatic acids tyrosine, tryptophan, phenylalanine, and, to a lesser extent methionine (Rinderknecht, 1986). The alkyl esters of these amino acids are also hydrolyzed, as are amides of substituted anilides. The specificity of all three chymotrypsin isoforms (A, B, C) is widely overlapping, with the exception that chymotrypsin C shows an increased ability to hydrolyze peptide, ester and amide bonds of the branched chain amino acids, leucine in particular. Accordingly, the preferred embodiment in a metaprobe designed to act as a substrate for all the chymotrypsins calls for leucine and its analogs as the tracer core. The optimal release tag in this configuration of tracer core is an isotopic label in the skeleton of the tracer core, and preferably at the carboxyl. Given the preference of chymotrypsins for aromatic amino acids, the preferred Derivative Complex consists of N-terminal peptides of the tracer core with the aromatic amino acids, in particular, tyrosine and phenylalanine in addition to a suitable carboxyl substituent on the tracer core, taken from the structural candidates listed in Table 4, but also including the carboxamides with 4-aminobenzoic acid and 4-aminophenylsulfonic acids. A schematic representation of this metaprobe is depicted in FIG. 7.

In a preferred embodiment of the method of the invention, these metaprobes are used as follows: the metaprobe is dispensed orally into the stomach of the test subject (or animal). In the absence of chymotrypsin, an event indicative of exocrine pancreatic insufficiency, the tracer core remains intact and the release tag is not subsequently available for detection, indicating pancreatic exocrine insufficiency and disease. Under normal conditions of pancreatic function, the metaprobe, which would otherwise pass through the digestive system unmetabolized, is hydrolyzed by pancreatic chymotrypsins. The liberated leucine analog (i.e., the tracer core) is absorbed and rapidly metabolized by the splanchnic bed, whereupon the release tag is liberated as $^{13}Co_2$ into the peripheral circulation and is ventilated by the lungs. Alternatively, the isotopic enrichment of the tracer core can be determined by isolating it from plasma or from other tissues and evaluating the tracer content directly by any suitable analytical technique.

The relative speed with which the metaprobe is hydrolyzed and the proportion of its dose that is cumulatively hydrolyzed overtime can be computed by pharmacokinetic, numerical evaluation of the $^{13}CO_2$ release tag or tracer core enrichment-time curve, thereby affording a proportional index of chymotrypsin enzymatic activity and gradations therein between and among subjects, with varying degrees of pancreatic secretory activity, and in a manner sufficient to differentiate between normal and abnormal pancreatic function (Goldberg and Durie, 1993).

Beyond gastroenterological applications, metaprobes specific to chymotrypsins are also functional substrates for enzymes that coincidentally share their substrate specificity but are not enzymes of pancreatic origin. Thus, in another aspect of the invention, a specific metaprobe is administered in such a way so as to direct it to a specific source or pool of the desired gateway enzyme in the subject. This aspect is pertinent when one is testing, e.g., one important class of these chymotrypsin like-enzymes, which are also gateway enzymes in Class III, the family of chymases that mediate angiotensin conversion under conditions of chronic therapeutic use of angiotensin converting enzyme inhibitors (Liao and Husain, 1995). The administration of metaprobes specific to chymotrypsin by routes of administration that bypass the pancreas and contact with pancreatic proteases, i.e., by intravenous, subcutaneous, intramuscular, intrabronchial or transdermal delivery, may be used to titrate in a similar manner the chymase capacity of the test host.

Another important class of chymotrypsin-like gateway enzymes involved as mediators of pathophysiological states in skin (Havima, et al., 1994) and along the submucosa of airways in the respiratory tract (Welle, 1997) are chymases associated with systemic mast cells. Mast cells regulate the immediate-type hypersensitivity reaction in non-allergic immune disorders as well as in normal physiological regulation of neuropeptide activity, bronchomotor tone and fibroblast mitogenesis (Holgate, 1997).

A representative chymotrysin metaprobe was synthesized by reaction of N-acetyl-L-phenylalanine with L-leucine [1-$^{13}$C], the latter protected as the carboxylamide with p-aminobezoic acid ethyl ester. Dosages of 1.5 mg/kg dissolved in 60 ml of ENSURE+ (a liquid meal) were dispensed to a cohort of probands considered normal with regard to digestive function and to a cohort suffering from pancreatic insufficiency secondary to alcoholic liver disease. The appearance of release tag was monitored and analyzed as described in Example I, but the test criterion was taken to be cumulative recovery of tracer as a percentage of dose two hours after ingestion. Normal subjects exhibited a Recovery Score of 69+/-15 per cent (n=3), while subjects with maldigestive compromise, attributable to insufficient pancreatic trypsin secretion afforded a Recovery Score of 22+/-11 (n=3), indicating that the metaprobe score provided a statistically significant differentiation in status both in accordance with clinical presentation and consistent with the principles of metaprobe operation for the chymotrypsin gateway enzyme system.

EXAMPLE V

Use of the Method of the Invention with γ-glutamyl Transpeeptidase (GGT)

Figure 2:
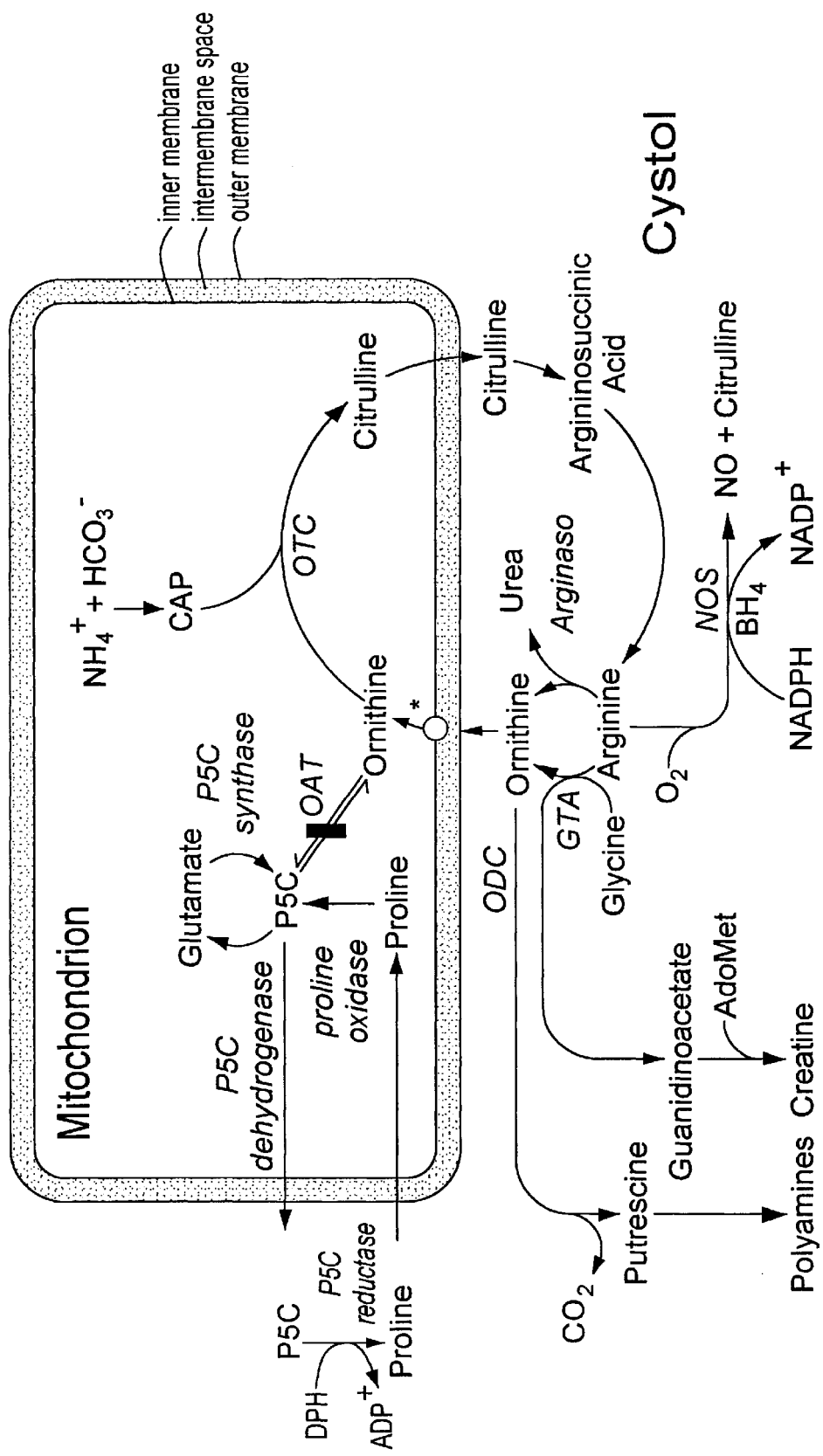
FIG. 2 illustrates gateway enzymes in the arginine/nitric oxide signaling pathway.

As shown in FIG. 1a, this membrane-bound enzyme transfers the glutamyl moiety of extracellular glutathione to acceptor substrates and therefore mediates the release of cysteine as well as the glutamyl-S-peptides into cells. It is the gateway into the γ-glutamyl cycle, the metabolic pathway that accounts for the enzymatic synthesis and degradation of glutathione. Glutathione itself is essential to the maintenance of cellular antioxidant status. It participates in providing reducing equivalents for many biosynthetic processes and is also a major substrate for the conjugative disposal of eicosanoids, carcinogens, toxins, and other mediators of inflammation and allergic responses (Allison, 1985; Tate and Mesiter, 1985)

Specifically, the properties of GGT as a gateway enzyme permit its use as a marker for proliferating tissue during pre-neoplastic transformations. GGT has been tracked in patients with breast cancer (Durham et al. 1997), melanoma (Benathan 1997), and small cell carcinoma (Ohlhauser et al. 1997). The temporal properties of its change in tissue concentration and in whole-body activity are also being exploited diagnostically as indicative of the status of cell differentiation and cell aging. For example, high enzyme activity is seen in cells of organs that participate in intense secretory or absorptive functions, such as epithelial canalicular, acinar and ductule cells, in the gut, kidney and liver. GGT titer is associated with the outcome of liver transplantation (Hasegawa, et al., 1997), the severity of liver dysfunction consequent to gastrointestinal malabsorption syndromes (Picot et al 1997), the response to oxidative stress in children with lung injury (Hull et al., 1997), the course of alcoholic liver disease (Bellini et al., 1997; Bianchi, 1997), and, more significantly the susceptibility to treatment for viral hepatitis (Colombatto et al., 1997; Laghi et al., 1997; and Pawlotsky et al., 1998). Therefore, using the method of the invention to assess GGT capacity in the whole body, or in selected organ systems accessed by different routes of metaprobe administration, will provide valuable insight into the success of therapeutic intervention in specific disease conditions, whose severity is already associated with changes in GGT activity.

In the prior art, numerous substrates for GGT have been explored by classical enzymological techniques in vitro and by radiotracer methods in vivo in which test animals are sacrificed, their organs and tissues disaggregated, and the concentration of GGT metabolism product identified by radiography and radioscintillation (Meister, 1985, 1989). These experiments afford a point of departure for determining a useful structure for a GGT metaprobe. It is known that glutathione analogs, both tripeptides and dipeptides, serve as GGT substrates, provided that their N-terminus consists of a γ-glutamyl moiety (which may be racemic or either enantiomer and structural analogs thereof) linked to cysteine or an isostere, serving as the preferred tracer core, the preferred embodiment of the latter being 2-aminobutyric acid labelled in its carboxyl group as the preferred form of release tag. This dipeptide may, in turn, be linked to glycine, a necessary component to maintain substrate binding to the GGT active site. For purposes of modulating absorption and distribution of the metaprobe, both the C-terminus and the N-terminus carboxyl may be protected by hydrolyzable substituents, as described in Table 4, in order to complete the carrier complex structure.

In addition to the tripeptide and dipeptide configurations of this metaprobe, a minimal metaprobe configuration consists of the γ-glutamyl moiety attached via an amide linkage to a suitably derivatized analog of 4-amino-benzoic acid, a molecule also known to be a general substrate for the evaluation of transglutamylation biochemistry (Szewczuk and Wellman-Bednawska, 1978). In this latter case, the glutamyl substituent itself serves as the tracer core, labelled at either the 1 or the 5 carboxyl groups, which, in turn, become the release tags.

A schematic representation for the GGT metaprobes is depicted in FIG. 8. These configurations include the known glutathione analogs, ophthalmic and norophthalmic acid, and their analogs whose methods of synthesis follows classical approaches for peptide synthesis, the exception being incorporation of a tracer labelled isotopolog as the tracer core substituting for cysteine (Douglas, 1989; Cobb et al. 1982). In all the three embodiments of this metaprobe, the tracer core is intended to bear the isotopic release tag, preferably as $^{13}$C in the carboxyl group. Although carboxyl labelled 2-amino-butyric acid is the preferred tracer core in the tri- and dipeptide configurations, carboxyl labelled glutamic acid may also serve as an alternate tracer core in all three configurations.

Both 2-amino-butyric acid and glutamic acid are preferred in this function, because their subsequent metabolism permits rapid generation of the release tag into plasma and breath. In the case of 2-aminobutyric acid, it does not enter into the protein synthesis reservoir and is rapidly transaminated to 2-ketobutyric acid which immediately enters the pathways of decarboxylative intermediary metabolism. In the case of glutamic acid, transaminative exchange is rapid and a ubiquitous intracellular reaction that affords 2-ketoglutaric acid, a key intermediate in the Krebs cycle and a principal contributor to the production of $CO_2$ as the end product of oxidative metabolism. No other tracer cores are known to be metabolized as fast as these two in mammalian systems.

The three forms of GGT probes provide diagnostic tools with a spectrum of specificities. The tripeptide form of the GGT metaprobe serves exclusively as a substrate for GGT. The dipeptide form offers a broader and additive picture of activity within the T-glutamyl cycle because its metabolism is indicative of the combined enzymatic activity of GGT and glutamylcyclotransferase, an enzyme that can also liberate the tracer core from the dipeptide metaprobe structure but not from the tripeptide structure. Application of the monopeptide metaprobe, by extension, provides metabolic information about all transglutamylation enzymatic steps with the body including the activity of GGT and cyclotransferase. Thus, through the sequential use of each of these three metaprobes, there can be obtained a fractional measure of GGT versus total glutamyl-interconversion biochemistry. This fractional measure can then be correlated, compared or contrasted to the fractional measures so obtained under different physiological or pathophysiological conditions.

The differential use of homologous metaprobes, to characterize physiological biochemistry from the specific to the general within a family of enzymatic reactions, is itself a novel implementation of the metaprobe concept. These non-limiting illustrations of the interoperability of metaprobes, as specific substrates for fundamentally different gateway enzymes that are accessed by virtue of the mode in which the metaprobe is dispensed, constitutes yet another embodiment to this invention.

A representative GGT metaprobe was synthesized and tested in an animal model system. L-2-amino-butyric acid, protected as the carboxylamide with ethyl p-aminobenzoate, was coupled with 2-acetyl-L-glutamic-1-ethyl ester via mixed anhydride activation (Bodanszky and Bodanszky, 1994). The resulting dipeptide was purified by column chromatography and then crystallized to afford a colorless solid, mp. 264–265. Four male New Zealand rabbits were treated with 2 mg/kg of this GGT metaprobe by intravenous injecton, and respiratory gases were collected for isotopic analysis over a three hour period. Sixteen hours after the first metaprobe breath test, the animals were treated to a glutathione depletion stress consisting of a 50 mg/kg bolus of acetaminophen and 50 mg/kg of cyclophosphamide, once an hour for 3 hours. One hour theratfer, a second intravenous GGT metaprobe test was carried out, followed by a three hour breath sampling period.

The appearance of release tag was monitored and analyzed as described in Example I. Noncompartmental analysis of the release tag impulse-response curve, based on oxidation of the 2-aminobutyric tracer core and $^{13}CO_2$ release tag post metabolism, and calculation of the fractional catabolic rate-dependant Metabolic Rate index for metabolism in peripheral tissue afforded the following scores: 175+/–58 nMol/kg/min for the control period prior to toxicological stress and 987+/–134 for the post stress period. This result indicates that the GGT metaprobe test functions as postulated by the theory behind its design and provides a sensitive measure for the degree of insult provided by glutathione-depleting drugs used in chemotheraphy and that it can be used a gauge for quantitating the biochemical response, and therefore, tolerance, to the dose intensity of such drugs.

EXAMPLE VI

Use of the Method of the Invention with Nitric Oxide Synthase (NOS) (FIG. 3)

Nitric oxide has been shown to be the principal cell signaling effector in a multitude of pro-inflammatory conditions (Packer 1996, Part B). It regulates vascular tone and triggers many acute phase reaction cascades associated with trauma and sepsis, as well as the more subtle metabolic dysregulation associated with free radical attack and oxidant stress in endocrine (Oberley, 1989), neuromuscular disorders (Simonian and Coyle, 1996), and immune-related diseases (Cook and Cattell, 1996). Because the fate of nitric oxide is extremely complex as it becomes embedded in multiple biosynthetic pathways of radical interchange before being converted into a stable, oxidized end product, namely, nitrate (Beckman and Koppenol, 1996), conclusions drawn about the magnitude of NO production or of its therapeutic regulation in a living organism, especially humans, cannot be addressed by measurement of excreted nitrate (Castillo, et al. 1994, 1995; Beaumier et al, 1996). Similarly, a plethora of analytical techniques, both spectroscopic and immunochemical, do afford quantitative information about NO biosynthesis in vitro, but they are all inadequate for doing so in vivo (Packer, 1996, Part B). Genetic markers may also be dismissed as quantitative tools in so far as they do not address the phenotypic properties of precursor-product conversion and their temporal interrelationships in real time.

Because of these limits in available methodology for the in vivo monitoring of NO production, especially during the course of diseases affected by NO overproduction, an alternative approach was developed to estimate the upper limit of NO production. Since arginine is the natural precursor and substrate for NOS and both NO and citrulline are the two end products of that conversion, it has become possible to measure the whole body process by which NO is produced in terms of quantitatively tracking the conversion of arginine to citrulline, using tracer probes incorporated into the guanidino group of arginine. Accordingly, control studies in humans undergoing nutritional status evaluation now have validated that the conversion of L-arginine[guanidino-$^{15}N_2$] to L-citrulline[ureido-$^{15}N_1$] matches the concomitant production by NOS of $^{15}NO$ (Castillo, et al., 1996; Lagerwerf et al., 1998). Unfortunately, the experimental mechanics for doing so involve a complex series of primed constant infusion studies and a complex series of secondary, control experiments that must be carried out in order to correct both the rate of arginine disappearance that is attributable to its cycling through the protein biosynthesis pool and the rate of citrulline appearance that is a result of de-novo synthesis from ornithine and not from the action of NOS.

The entire exercise of deconvoluting the fate of citrulline derived from arginine via the NOS pathway can be greatly simplified first by the use of more effective data reduction procedures based on compartmental deconvolution as described in Example III and, more importantly, through the use of improved metaprobes designed specifically in accordance with the principles espoused in this invention.

Figure 9:
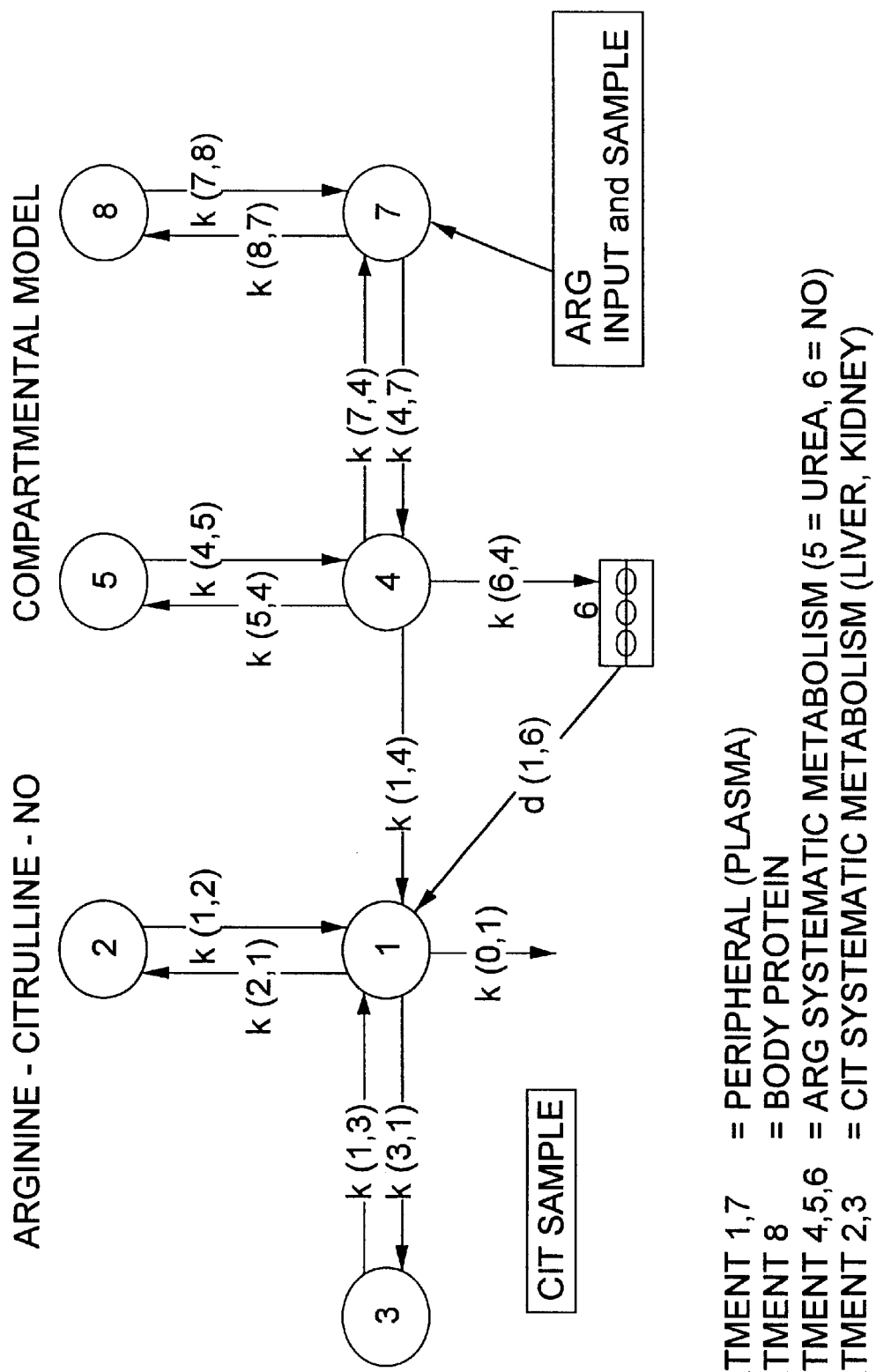
FIG. 9 illustrates a compartmental model for the relationship among arginine, citrulline and nitric oxide.

When L-arginine[guanidino-$^{15}N_2$], which is in effect a minimal metaprobe comprised of ornithine as the tracer core and the guanidino substituent as the release tag, is administered intravenously, either by bolus or by short-term infusion, the temporal properties of citrulline and arginine appearance are accurately described by the compartmental model depicted in FIG. 9. Although not recognized in the prior art, it follows from this model that a useful index of NO production (NOPI1) is defined as: NOPI1=CFSR×AREC, where CFSR is the citrulline fractional synthesis rate per kg body weight per hour via NOS from the compartmental model, corrected for the delay in rate of appearance, i.e., k(6,4)×d(1,6), and AREC is the amount in micromoles of arginine metaprobe recovered as citrulline after a period corresponding to 10 times the arginine metaprobe's plasma half life.

A further refinenement, designed to correct for interindividual differences in arginine flux, consists in normalizing NOP1 as a percent of arginine flux so that: NOPI2 = 100*NOPI1/QA, where QA is the arginine plasma replacement rate computed by non-compartmental analysis of arginine residual enrichment versus time curve, the latter having been extrapolated also to 10 times the arginine metaprobe's plasma half life.

The NOPI index obtained in this manner represents an advance over the data interpretation schemes in the prior art (Castillo, et al., 1996; Lagerwerf et al., 1998) and can be used to characterize the NO production status, and, by extension, the oxidant stress load of patients who otherwise cannot be easily stratified on the basis of this underlying biochemical insult. Table 6 illustrates the relationship between the NOPI2 and the status of both normal control subjects and patients examined on admission to critical care for treatment of sepsis or complications from surgical trauma.

These studies constitute part of a continuing series intended to extend the protocols initiated by Castillo et al. (1996) and depend on intravenous metaprobe administration and mass spectral analysis of the resulting analytes extracted from plasma. They show both a statistically significant ($p<0.01$) difference in NO production status between normal controls or uneventful admissions to critical care and more complicated treatment cases that required a greater extent of hospitalization and exhibited greater morbidity and mortality. The timely use of the NOPI2 index as described in this invention in the future will permit the scheduling of more aggressive treatment for candidate patients who are suffering a predictable risk of complications from an elevated, and potentially unchecked, level of NO production at the outset of their hospitalization.

TABLE 6

Nitric Oxide Production Index (NOPI2) and Clinical Status/Outcome

| GROUP | NOPI2 on Admission | OUTCOME |
|---|---|---|
| Normal Control | 0.2 +/− 0.15 (n = 4) | Healthy (not admitted) |
| 2 day average in ICU | 0.3 +/− 0.14 (n = 4) | Rapid recovery, no sepsis |
| 4 day average in ICU | 2.99 +/− 1.24 (n = 4) | Recovery, sepsis treated successfully |
| 7 day average in ICU | 6.64 +/− 1.92 (n = 3) | Death from complications of sepsis and trauma |

Notwitstanding the usefulness of the methodology just described, there remains considerable analytical complexity required to obtain the kind of results illustrated in Table 6. Such a potential drawback militates in favor of implementing a similar protocol with metaprobes that are intrinsically more amenable to rapid analysis and that adhere to simpler models for data deconvolution. Thus, preferred embodiments of the NOS metaprobe concept with greater potential clinical utility consist of arginine analogs which are known NOS substrates but do not participate in any subsequent biosynthetic processes, either prior to their conversion into ureido species, or thereafter through the various recycling processes that both citrulline and arginine are subjected to in vivo. These improved metaprobes, illustrated in FIG. 10, include the lower and the higher homologs of arginine, e.g., homoarginine, and a spectrum of therapeutic guanidino drugs, e.g., 5-guanidinovaleric acid, that are known to be substrates of NOS. In these structures, the tracer core can be taken from among homologs or analogs of ornithine and other suitably substituted alkyl amines that can maintain an affinity with the NOS active site domain (Hecker et al., 1991; Yokoi et al., 1994; Crane et al., 1997; Deshmukh et al., 1997). A release tag is then attached by guanidinylation of their corresponding free amino groups with a suitable reagent that affords either a $^{15}N_2$ or a $^{13}C$ or a $^{13}C$-$^{15}N_2$ guanidine or hydroxyguanidine. Subsequent functionalization of any remaining carboxyl groups yield the completed carrier complexes as depicted in FIG. 10.

Metaprobes of this design can then serve as more efficient in vivo substrates since their conversion by NOS from guanidines to the corresponding ureido species can now be traced more directly in so far as these metabolites are more biologically stable and non-recycling end products than their congeneric citrulline analogs. Further, unlike in the case of the arginine derived metaprobes, computation of the corresponding NOPIL values for the metabolism of the structures shown in FIG. 10 will not require recalculation of the NOPI2 value. Normalization to the flux of metaprobe is no longer a necessity because in the absense of metabolic recycling there is no need to compensate for interindividual variations in the disposal of the parent metaprobe itself. Thus, the improved metaprobes offer a "one shot" kinetic profile in their conversion by NOS, and, therefore, can expedite both the computation and the specificity of the NO production measurement in those same clinical contexts as were examined in Table 6. Moreover, any expedited protocols for determining NO status would then permit application of these tools in an outpatient setting, both to follow the course of disease and the efficacy of antioxidant therapy, thereby expanding the scope of utility to include patient populations in whom NO oxidant stress is a contributor to increased morbidity caused by atherosclerosis, respiratory distress, cystic fibrosis, cataracts, macular degeneration, neurological disease (Parkinson's, Alzheimer's amyotrophic lateral sclerosis, non-alcoholic liver disease, diabetes, connective tissue damage (Sies, 1997) and pancreatitis (Tsai et al., 1998).

EXAMPLE VII

Use of the Method of the Invention with Cystathionine Synthase (CS) and α-ketoacid Decarboxylase (KAD)

In the last ten years, the biological chemistry of thiols in vasculature and in vascular-related disease has attracted overwhelming attention in the field of cardiology in so far as the alterations induced by oxygen free radicals are not only the causative agents of direct myocardial damage but also principal contributors to the development of arterial occlusive disease (Stamler and Slivka, 1996). One of the more significant interactions of free radicals (Sies, 1997; Ferrari et al., 1998) is with homocysteine, an intermediate in the methionine-cysteine remethylation pathway shown in FIG. 3. It is now, therefore, axiomatic that inability to clear homocysteine from the body, either through the vitamin $B_{12}$ and folic acid requiring pathways of methionine resynthesis or via metabolism through the cystathionine synthase gateway enzyme system, is a preponderant risk indicator for subsequent morbidity and mortality. For example, high plasma levels of homocysteine predict mortality in patients with angiographically confirmed coronary artery disease (Nygard et al., 1997), are a common finding in psychogeriatric populations suffering from dementia of vascular cause (Nilsson, 1996), and accompany the premature atherosclerosis of non-insulin dependent diabetics (Fonseca et al., 1998), especially among obese and elderly patients. Changes in the host's capacity for homocysteine synthesis and breakdown also correlate with the effect of aging on connective tissues, lipid synthesis, auto-immune diseases and carcinogenesis (McCully, 1994).

Current approaches for assessing homocysteine clearance are fall into two classes: a) genotypic assays aimed at predicted the individual's genetic propensity for homocysteinemia by identifying gene mutations or deletions, such as those governing the folate dependent thermolabile isoforms and b) static assays of plasma levels either by conventional chromatography or by isotope dilution mass spectrometry (Allen et al., 1990, U.S. Pat. No. 4,940,658; Allen et al., 1994, U.S. Pat. No. 5,374,560; Allen et al., 1995, U.S. Pat. No. 5,438,017). In this latter case, the result is a static plasma value and not a measure of production capacity, and presents with wide variations depending on the dietary history of the host. The more effective assay procedures are organized around a stimulatory event such as a methionine load, the theory of operation being that this extraordinary input of methionine (100 mg/kg) orally will "swamp" the various enzymes in the methionine-homocysteine-serine pathways and that those individual who cannot clear homocysteine fast enough relative to controls will then present with abnormally high plasma concentrations. The novel approach taken in this invention draws on the metaprobe concept, in an analogous manner to the schemes presented in Example I. Instead of merely examining static plasma levels, the use of a metaprobe permits direct assessment of the capacity to clear homocysteine, both before and after methionine load.

The principle of the test is to quantify the metabolic throughput of homocysteine metaprobe through the cystathionine synthase (CS) gateway, also known as the transulfurization pathway. This enzyme converts homocysteine and serine into cystathionine. Its K is the lowest in the cycle, consistent with the definition of "gateway" enzymes, and, therefore, serves as the metabolic entry to the irreversible disposition of homocysteine, since, once past the gateway, homocysteine can no longer participate in the remethylation cycle. Cystathionine is rapidly converted by cystathionase to cysteine and 2-aminobutyric acid (ABU), the latter bearing the carbon derived from the homocysteine skeleton. ABU, in turn, is rapidly transaminated to α-ketobutyric acid and then rapidly oxidized by the KAD gateway enzyme system into $CO_2$, which can be measured in breath. The $K_m$ values of both cystathionase and of the subsequent enzymes responsible for ABU degradations are two orders of magnitude higher than the values of cystathionine synthetase and, therefore, cannot be saturated by products of transulfuration.

In this invention, the rate of substrate metabolism through the CS gateway is accomplished in two ways. In Method 1, the metabolism of homocysteine itself is monitored directly with homocysteine metaprobes. In Method 2, the metabolism of homocysteine's principal non-recycling metabolite, namely ABU, is monitored by means of a KAD metaprobe that is structurally related to the products of the CS gateway enzyme.

In Method 1, homocysteine itself can be used as a tracer core, with labeling in any carbon group at the 1,2,3, and 4 position of the molecule, the preferred release tag being $^{13}CO_2$ incorporated into the carboxyl terminus. Because homocysteine and, especially, its thiolactone are both toxic and unpredictably reactive materials, these cannot be dispensed safely without derivatization into a suitable derivative complex, whose hydrolysis subsequent to dose administration will then serve as a form of controlled release of homocysteine to its site of metabolism. FIG. 11a depicts the metaprobes of greatest utility for direct measurement of homocysteine metabolism, which comprise a family of cyclic intermediates. Class A are oxoprolinase substrates, consistent with the structures illustrated in Example III, and generally synthesized by N,S cyclization with phosgene, ethyl chloroformate or a similar bifunctional carbonylating reagent. Class B are functionalized thiazolines formed by cyclodehydration of the free sulfhydryl and the free amine with a suitable aldehyde or ketone. The embodiments of Class B are known to hydrolyze spontaneously in plasma, thereby serving as a controlled release mechanism for the trecer core and release tag.

For Method 2, the prefered embodiments are KAD metaprobes constructed from aminobutyric acid and its derivatives labeled with carbon at any (or all sites), as shown in FIG. 11b. Metaprobes in this class find their preferred use as breath test substrates, when applied in accordance with the general procedures outlined in Example I. Two pilot studies were performed to illustrate their utility. In study 1, a BASAL measurement, CS activity was determined using the metaprobe L-2- oxo-tetrahydro-1,3-thiazine-4-carboxylic acid ethyl ester. The metaprobe was synthesized by phosgene cyclyzation of L-homocysteine[1-$^{13}$C] ethyl ester and isolated as a crystalline material, which afforded a sterile and pyrogen free solution after formulation and 0.22 micron ultrafiltration under aseptic conditions. An intravenous bolus of 2 mg/kg into was dispensed into male New Zealand rabbits according to standard procedures for conducting breath tests on small animals (Mohan et al., 1991). Breath collected in 10 ml evacuated containers at 5, 10, 15, 20, 25, 30, 45, 60, 75, 90, 105 and 120 minutes was analyzed by isotope ratio mass spectrometry and the resulting impulse response curve analyzed compartmental modeling (Wagner, 1993; Barrett, 1998). The temporal properties of the metaprobe metabolism were well suited to analysis as a two compartment open model with elimination from the central compartment after a delay period. A metabolic index was constructed, as in Example III, namely, the derived fractional catabolic rate in the peripheral (tissue) compartment multiplied by the dose of tracer metaprobe adjusted for the percent of isotope release tag recovered, using for this latter computation the area under the tracer-in-breath exhalation profile extrapolated to a time equal to 10 half-lives based on the 13CO$_2$ excretion rate constant. The next day, animals were preloaded by five small enteral feedings totaling 100 mg/kg of methionine dissolved in carrot juice and ingested over 0.5 hours. Two hours after consumption of the methionine challenge load, the metaprobe breath test was repeated. Table 7 shows the results of this MET+ test in comparison to the previously obtain BASAL values. LI, the load tolerance index, is defined as BASAL values minus the subsequent MET+ test score.

TABLE 7

CS Gateway Enzyme Gateway Breath Test in Rabbits Treated With Homocysteine Metaprobe

| GROUP | Metabolic Response Index (MRI) in MicroMol/kg/hr. |
|---|---|
| BASAL | 85 +/− 14 (n = 4) |
| MET+ | 28 +/− 16 (n = 4) |
| LI | 57 +/− 24 (n = 4) |

These findings are consistent with the underlying physiology of normal homocysteine clearance. Under basal conditions, the metaprobe is not diluted as much by the endogenous homocysteine. Hence, upon passage through the CS gateway, the metaprobe is metabolized in higher proportion than the endogenous substrate. Upon methionine load, more homocysteine is generated but not cleared quickly by either the easily saturated CS pathway or the transmethylative routes, thereby causing a transient homocysteinemia which dilutes the exogenous metaprobe to a significant greater extent. The dilution is reflected in the subsequent lower appearance of tracer release tag in breath characterized by the lower MRI test score. It follows that the LI value then represents a measure of the detoxifying capacity for homocysteine. Using this approach, a dynamic normative database can be generated as the basis for prognosis and management of disorders of homocysteine metabolism. Thus, individuals presenting with BASAL values lower than the norm and those unable to respond to methionine loads with a sufficiently high LI value to be considered "normal" can be indentified as belonging to a higher risk population, even at a time when they are asymptomatic for the overt, deleterious health effects implicit in the dysregulation of homocysteine clearance.

It should be noted further that an even simpler screening tool for homocysteine clearance regulation after a methionine challenge can be constructed using the KAD metaprobes shown in FIG. 11b. One of the preferred embodiments is a metaprobe constructed as the N-acetyl-ABU, with the release tag in the carboxyl group. This non-proteinogenic aminoacid is a safe natural product. Its oral ingestion leads to rapid absorption and rapid first pass metabolism by mitochondrial ketoacid decarboxylases in the liver, as described previously in Example V, and it is more than 70% cleared from the system in two hours. In a pilot trial, 2 mg/kg of this metaprobe were ingested by an adult male in the fasting state. The metaprobe was dissolved in 50 ml of orange juice. Breath samples were taken at periodic intervals over 2 hours. After an additional hour's rest period, the same subject ingested 100 mg/kg of methione in 50 ml of orange juice flavored with Angostura bitters, to mask the aftertaste of methionine. Again breath samples were monitored over two hours. Analysis by isotope ratio mass spectrometry of the enrichment in breath showed a biexponential rate of release tag appearance in breath, after an absorption phase whose kinetic order could not be characterized. The impulse-response curve was processed by compartmental deconvolution (Wagner, 1993) to afford mean residence times for metabolism in the central compartment (MRTC) and in the entire system (MRTS). MRTS-MRTC afforded a measure of metabolism in peripheral tissue (MRTP). As before, a metabolic rate index (MRI) was constructed according to the equation MRI=Dose×$^{13}$C-Recovery×1/MRTP. The experiment was repeated three times over a period of three weeks with the following results, shown in Table 8.

TABLE 8

CS Gateway Enzyme Gateway Breath Test in Man Treated With Aminobutyrate Metaprobe

| GROUP | Metabolic Response Index (MRI) in MicroMol/kg/hr. |
|---|---|
| BASAL | 145 +/− 24 (n = 3) |
| MET+ | 105 +/− 26 (n = 3) |
| LI | 40 +/− 9 (n = 3) |

Again, the findings are consistent with the KAD metaprobe's mode of action, in this case as an index of the metabolism of ABU when the CS gateway, a predecessor in the cystathionine clearance cascade, is overloaded. Taken as a combination, both these approaches to characterizing the regulation of homocysteine disposal offer a suite of sources for differential information about the metabolic effects of homocysteine pathophysiology and, therefore, can be used as prognostic and therapy management tools in interventions aimed at restoring homocysteine homeostasis to within normal values in patients whose dysregulation of this pathway is under consideration. Not only are these findings consistent with the results obtained by the standard loading protocols with either homocysteine (Guttormsen et al., 1996) or methionine (Bostom et al., 1995), but they are less invasive to perform than serological tests and have the overwhelming advantage of providing dynamic metabolic information rather than static plasma levels.

EXAMPLE VIII

Use of the Method of the Invention with Glutamine-fructose-6-phosphate Aminotransferase (GFT) and Liver N-acetyl Transferase (NAT)

In recent years, the diabetic population worldwide has increased steadily to such an extent that non-insulin dependent diabetes (NIDDM) can be viewed as a disease of epidemic proportions, especially when considered with the aggregate effect on morbidity and mortality of its collateral coronary artery disease. The importance of NIDDM as a negative cost factor in health care has prompted an accelerated search not only for antidiabetic drugs that can alleviate its impact (Ammon et al., 1996), but on the root causes. A link between free radical mediated oxidant stress and insulin dependent diabetes (IDDM) has been convincingly established in so far as NO mediated redox signaling leads to the self-destruction of insulin producing islet cells (Sies, 1996). For example, DNA strand breaks and activation of nuclear enzyme poly-ADP-ribose polymerase are prominent consequences of oxidant radical islet cell damage. In the case of NIDDM, the links between oxidant stress and dysregulation of insulin efficacy and/or increased glucose toxicity still remain to be established except as coincident phenomena. The elderly and the obese, both of whom as classes of patients are most likely to sustain insults from oxidant stress, also present with the highest incidence of NIDDM. Moreover, approximately 15% of NIDDM cases will become insulin dependent, so that there exist commonalities in the underlying pathophysiology of both diabetic presentations.

One of the regulatory processes currently under aggressive investigation as a causative agent both in islet cell dysfunction, i.e., insulin production, and in insulin signal mediation, i.e., insulin sensitivity and resistance, is the encoding for and genomic control of glutamine-fructose-6-phosphate aminotransferase (GFAT) (Shankar et al., 1998) (see FIG. 4). As described in the introductory remarks to Example II, this enzyme is the limiting gateway for the production of glucosamine (McClain and Crook, 1996). GFAT overexpression leads to overproduction of glucosamine and the subsequent disruption in cell signalling, caused by over-glycation in the transduction mechanisms for growth factor, transporter, and receptor protein biosynthesis, and ultimately mediates the toxic effects of hyperglycemia and insulin resistance, the hallmark of both IDDM and NIDDM. GFAT is expressed in most human tissues involved in the development of late diabetic complications, such as adipose and skeletal muscle where the effects of insulin resistance are most acutely manifested (Nerlich et al., 1998). It is also strongly expressed in vascular smooth muscle cells, nerve sheath cells, and in mesangial cells, where glucosamine mediated disruption of signaling pathways can be explained as the pathomechanic link between hyperglycemia and the overt vascular, motor, and renal pathology of diabetes.

The potentially pivotal role of GFAT has triggered numerous investigations in the development of anti-diabetic agents targeted at GFAT molecular, genetic patterns of expression (McKnight et al., WO 93/21330, 1993; Ammon et al., 1996; Nishi et al., EP 0 824 149 A2, 1998). In this present invention, the focus is on a more physiological and phenotypically utilitarian approach based on direct evaluation of glucosamine production and disposal capacity, rather than on genotypic assessments. The method of the invention is also a dynamic one, dependent on measuring an individual's capacity to maintain glucosamine homeostasis and not just dependent for significance on measurements of a static nature, as exemplified by the kinds of serological tests in current use for just measuring glucosamine titers in individual tissues. The daily balance of synthesis and metabolism of glucosamine can be gauged by the simple expedient of using two metaprobes simultaneously: one for the purpose of determining the relative conversion of glutamine into glucoseamine via GFAT and another to serve as an index of the relative turnover of the glucosamine reservoir in the body, including all of the storage pools, whether of de novo biosynthetic or dietary origin, in glycoproteins and the many subsequent metabolites of glucosamine's incorporation into other metabolites after its acetylation via the NAT gateway enzyme system.

Figure 12B:
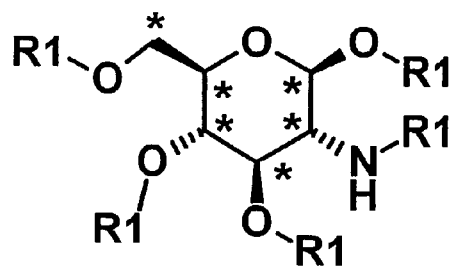
FIG. 12b depicts an exemplary set of metaprobes for glutamine fructose-6-phosphate amidotransferase (part 2).

Thus, for tracing glucosamine synthesis, the preferred metaprobes, shown in FIG. 12a, consist of glutamine and its analogs comprising the tracer core, with a 5-$^{15}$N-amide serving as the release tag and suitable derivatizing moieties at the 2-amino and carboxyl terminus, designed so as to insure a sufficient plasma half-life and subsequent delivery of intracellular glutamine. Such candidate derivatized forms of glutamine include N-acyl-conjugates with fatty acids and amino acids, carboxyl esters, carboxyl amides, and the other derivatives that are suitable carboxyl masking agents, as previously described in Table 4. The second metaprobe applied in this example to the NAT gatway consists of glucosamine itself, labeled with one or more $^{13}$C-atoms as the release tag, although deuterium and oxygen isotopes may also be employed, and functionalized into a carrier complex by N- and/or 0-acylation, the preferred embodiment being N-acetyl-glucosamine itself, as shown in FIG. 12b. This class of NAT metaprobe is intended to quantify the fate of glucosamine during biochemical events taking place after the point of synthesis at the GFAT gateway.

In the course of glucosamine synthesis, a measurable proportion of the $^{15}$N-release tag from glutamine is transferred to glucosamine, and the extent of release incorporation into glucosamine becomes a measure of glutamine utilization by GFAT. The resulting $^{15}$N-glucosamine then undergoes a complex series of subsequent metabolic transformations beginning with acetylation and subsequent transacetylation via NAT, progressing through the many stages of protein glycation, and ending with excretion into urine as a distinct class of end stage metabolic conjugates. Among these, the aspartyl-N-acetyl-glucosamine pyranoside (Maury, 1981) and the bile acid (glycocholic and taurocholic) glucosaminides (Marschall et al., 1989) are the more plentiful ones that are amenable to isotopic analysis by readily available mass spectral techniques. Accordingly, the second metaprobe to be co-administered, namely an analog of pre-formed N-acetyl-glucosamine itself and a substrate for the NAT gateway enzyme, bearing a $^{13}$C or another different isotopic release tag other than the one incorporated into the GFAT metaprobe, serves as an indicator for the size and extent of the existing glucosamine pools and their turnover rates once past the gateway of its initial transaminative biosynthesis. The NAT metaprobe shares the same metabolic fate as the newly synthesized $^{15}$N-product and then is excreted in the same manner, thereby affording a means by which de novo production can be normalized to the subsequent turnover of similar, but pre-formed material. The combination of the two metaprobes, where a) the product of a first gateway is then b) the precursor for another gateway in a sequence that c) culminates with the isotopic release tags of both being analyzed in a common excreted fraction, permits the computation of one or more suitable GFAT metabolic rate indices (GFAT-MRI) that can be normalized to background NAT gateway activity. These indices may be the result of compartmental modeling, conceptually along the lines described in Example VI, or a simple numerical expedient in which the fraction of the dose recovered from the GFAT (glutamine) metaprobe, i.e., the $^{15}$N-content in the urinary conjugate fraction, is normalized to the fraction of the dose recovered from the NAT (N-acetyl-glucosamine) metaprobe, i.e., the $^{13}$C content in the same excreted fraction.

The following two experiments are illustrative of the method and provide initial evidence of its feasibility as a method of metabolic tracing for GFAT in vivo by means of two distinct metabolic rate indices (MRI1 and MRI2). In the first experiment, six male Sprague-Dawley rats, weighing on average 300 grams, were studied while awake and unstressed after an overnight fast. N-acetyl-5-$^{15}$N-glutamine at a dose of 30mg/kg and N-acetyl-1-$^{13}$C-glucosamine at a dose of 5 mg/kg were prepared as a 10% (w/v) solution in 10% aqueous fructose corn syrup delivered by gastric intubation in four portions over a half hour period. Food and water were then given ad libitum. After receiving the metaprobes, the animals were kept in metabolic cages to facilitate collection of urine (Robinson, 1968). After 24 hours, the urine was concentrated by lyophilization, subfractionated by solid phase extraction on Sep-Pak C18 to obtain total bile acids, and then chromatographed by ion exchange to obtain the fraction of amidated bile acid glycosides. These were then hydrolyzed with N-acetyl-glucosaminidase and snail glucosidases according to literature procedures (Marschall et al., 1989).

The resulting glucosamine fractions were analyzed by combustion isotope ratio mass spectrometry in a calibrated system designed for conducting simultaneous mass balance studies on biological extracts of urine labeled with $^{15}$N and $^{13}$C (Browne et al., 1993, 1997). The percent of metaprobe dose recovered as $^{15}$N, indicating relative de novo glucosamine synthesis, was 0.036+/−0.015. The per cent recovery of $^{13}$C, indicating the relative dilution space for the N-acetyl-glucosamine metabolite, was 0.15+/−0.073. The resulting normalized $^{15}$N/$^{13}$C GFAT-MRI1 is then calculated as 100×0.036/0.15=24. Accordingly, any statistically significant elevation in this index would be evidence of excessive GFAT activity and could be evaluated longitudinally over the life history of disease treatment or in response to glucostatic challenges. Variations from normative values for control subjects in IDDM and NIDDM would be followed in a similar manner.

In a second experiment, a normal, 75 kg male subject, 48 years old, with normal blood glucose and triglyceride levels after an overnight fast, was dispensed an oral dose of 600 mg of N-acetyl-1-$^{13}$C-glucosamine and 100 mg dose of N-acetyl-1-$^{13}$C-glucosamine once an hour for four hours. The tracers were ingested each time with 100 ml of a 10% aqueous solution of high fructose corn syrup. Urine samples were collected at 12, 24 and 36 hours. Analysis for the aspartyl- N-acetyl-glucosamine pyranoside by combined gas chromatographic/mass spectrometric analysis (Maury, 1981) revealed an average urinary concentration of 1.8+/- 0.3 mg/Liter. Fragmentographic evaluation of the derived ion spectra, in comparison to reference spectra of individually labeled reference standards, indicated that both $^{15}N$ and $^{13}C$ were present in the urinary fractions. As in the previous demonstration of applicability, the relative recoveries of the two tracer release tags were expressed in terms of the $^{15}N/^{13}C$ ratio multiplied by 100, in order to obtain the normalized MRI2 values, shown in Table 9. The analysis of each urine sampling interval was carried out in triplicate and the variation among replicates fell within 15%. These data indicate an equilibration of the two tracer species after 24 hrs. and that a basal GFAT MRI2 can be computed within that time frame from a convenient oral dosing protocol in vivo. Also, since aspartyl-N-acetyl-glucosamine pyranoside is rapidly synthesized and subsequently turned over by lysozomes, its rate of appearance in plasma can be determined, along with the plasma rate of appearance of N-acetylglucosamine, at shorter intervals post dosing. Thus, the MRI2 index could be computed within reach of the two-hour preferred sampling time frame for the practicable implementation of diagnostic procedures with metaprobes.

This second approach and its variations in form of dosing, e.g., oral or intravenous, and site of sampling, e.g., plasma, selected blood fractions or urine, also represents a method whereby GFAT overexpression can be traced by virtue of its metabolic, rather than its genomic, signature. Identification of that signature prior to the onset of overt diabetic symptoms and subsequent modulation of that signature's magnitude by means of antidiabetic treatments, whose efficacy is titrated in step with changes in the GFAT metabolic rate indexes, are demonstrably obtainable objectives using the methods of the invention for probing gateway enzyme pathways.

TABLE 10

GFAT metabolic response index (MRI2) in human urine

| TIME POINT (hr) | 15N % Dose | 13C % Dose | Metabol. Resp. Index |
|---|---|---|---|
| 12 | .016 | .089 | 18 |
| 24 | .035 | .189 | 19 |
| 36 | .047 | .213 | 22 |

Based on the derivation of the MRI2 in Table 9, it is easily envisioned that a comprehensive set of MRI values for GFAT overproduction can be established, for example, by gender and by 5 year life history in asymptomatic individuals. These normative values would be available to clinicians for subsequent comparison and contrast to corresponding ones taken from individuals presenting with diabetes, both before and after the onset of diabetic complications. A normative, natural-history of GFAT activity through the course of adult life, or as a function of life style and putative exposure to the effects of oxidant stress, would then form a part of the decision making mechanisms in patient care as a prognostic index for future outcomes that are correlated with prematurely high GFAT MRI values. USE Cancer Treatment Management The number of new cancer cases has approximately doubled in the past decade due primarily to aging in the population. People over 65 are ten times more likely to develop cancer than those under 65. Changing technology, earlier diagnosis, and better treatment have increased the five-year survival rate of cancer patients from approximately 39% in 1963 to approximately 54% in 1991. This improvement in survival rates has increased the demand for cancer related services. The methods of the invention have application in answering this demand, for example, in managing the nutritional support needs of cancer patients and in precisely tailoring chemotherapy doses for specific patients to facilitate adaptation to chemotherapy regimens.

Cancer is a group of over 100 complex diseases characterized by the uncontrolled growth and spread of abnormal cells. Therefore, chemotherapy is often complex and requires careful management to minimize adverse side effects. The oncologist must strike a balance between doses high enough to kill fast growing cancer cells and those that would cause permanent impairment to the rest of the person. This balance is critical, since it has been shown for some cancers that a doubling of chemotherapy concentration in the tumor site can create a tenfold increase in treatment effectiveness. Generally, the oncologist is forced to apply "average dose" drug regimens, with adjustments only for body mass.

Breath biopsies using the method of the invention will allow patient tailored dosing to maximize treatment effectiveness and minimize overdose side effects. For example, the glutathione cycle can be measured dynamically to determine the patient's ability to withstand the shock of high dose chemotherapy. Resilient patients can receive heavier doses with better outcomes, and less resilient can receive lower doses, avoiding costly side effects, or receive alternative therapies, such as radiation. Furthermore, many cancer patients require nutritional support during their course of treatment. The use of breath probes in the method of the invention to assess body composition, energy expenditure and needs, and nutritional status can aid in managing dietary supplementation. This highly targeted approach can help minimize wasting, or cancer cachexia, a major obstacle to recovery in cancer patients.

Viral Load/Infectious Diseases

Viral load testing is a very helpful indicator of the assault intensity of pathogens in a given patient. However, such testing is at present conducted in a vacuum without a assessment of the patient's ability to withstand a given viral load. The effects of viral load are inversely related to cytoprotective capacity and antioxidant status, which are modulated principally by glutathione. Measurement of glutathione flux by the method of the invention will help determine likely responders to various therapies and allow more selective use of expensive antiviral treatments.

Therefore, treatment for patients with a number of infectious diseases and immune system disorders (including autoimmune disease) will benefit from the method of the invention. AIDS drug therapy, has evolved to include the concept of viral load as the method of determining appropriate drug regimens. For example, it has recently been reported that levels of glutathione in CD4 cells are "predictive of survival" for AIDS patients (Herzenberg et al., 1997).

The viral load concept is also becoming more relevant for management of patients with hepatitis. Glutathione probes in the method of the invention are able to differentiate patients with chronic active hepatitis and alcoholic liver disease (cirrhosis). Thus, the appropriate treatment for each condition can be provided to the patient.

Management of Diabetes

Diabetes is a disease in which the body does not produce or properly use insulin, a hormone that is needed to convert sugar, starches and other food into energy needed for daily life. There are 15.7 million people or 5.9% of the population in the United States who have diabetes. Based on death certificate data, diabetes contributed to more than 187,000 deaths in 1995. Diabetes is a chronic disease that has no cure. The total annual economic cost of diabetes in 1997 was estimated to be $98 billion dollars. That includes $44.1 billion in direct medical and treatment costs and $54 billion for indirect costs attributed to disability and mortality.

There are two major types of diabetes. Type 1 diabetes accounts for 5–10 percent of diabetes. This autoimmune disease, in which the body does not produce any insulin, most often occurs in children and young adults. People with Type 1 diabetes must take daily insulin injections to stay alive. Type 2 diabetes, or non-insulin dependent diabetes, accounts for 90–95 percent of diabetes. Type 2 diabetes is nearing epidemic proportions, due to an increased number of older Americans, and a greater prevalence of obesity and a sedentary lifestyle. As discussed in the Examples, the methods of the invention can make management of both forms of diabetes significantly easier.

Critical Care/Intensive Care Applications

High risk, high cost patients in ICUs, step down units, and cardiovascular units occupy 35% of US hospital beds and 50% of hospital coats. Assessments of such patients today, where they exist, include risky and expensive invasive approaches, empirical clinical observations, or non-patient specific computer algorithms. Apache Medical Systems, a software company that provides prospective management tools for such patients, believes that $20 billion in savings could be generated with better resource allocations. Use of the methods of the invention to obtain patient specific analyses will permit much better resource allocations for these patients than currently existing population-based indices.

For example, the methods of the invention allow patient-specific analysis that will be much better accepted by intensive medicine practitioners than population-based decision support systems such as those distributed by Apache Medical Systems. Tracer probes can be used to measure biochemical activity related to oxidant stress and the immune system response to provide early stage guidance for management of patients in intensive care units. To illustrate, seriously ill patients with comparable Apache scores have been shown to have widely divergent outcomes. The methods of the invention conceptually differentiate such patients with similar Apache scores by prognosis and allow proactive clinical interventions.

Neurodegenerative Disorders

Probes for early diagnosis of Parkinson's disease and Alzheimer's disease, among other neurodegenerative disorders, are also candidates for use in the methods of the invention. It is believed that these disorders have a connection to antioxidant stress and the gluthione/NO cycles described above.

For example, the triggering of programmed cell death by NO and its successor oxidant radical cascade is a principal causative agent of de-myelinating and depolarizing disorders that result from the gradual destruction and failed repair of neuronal and accompanying cells. Glutathione mediated antioxidant detoxifying mechanisms are the natural cytoprotectants, whose beneficial action can become irreversibly overwhelmed, so that diagnostic methods for monitoring both the progression of oxidant attack and the repletion of oxidant capabilities would be desirable tools in patient management, even at the early onset stages before full manifestation of clinical symptoms. Dementia, multiple sclerosis, and amyotrophic lateral sclerosis all could be managed more effectively if the management could be aided by objective, biochemical indices of antioxidant capacity both at the whole body level and in the most affected organ system. The use of the kinds of metaprobes described herein would be an appropriate, minimally invasible approach to obtain dynamic, biochemical information to augment the traditional static clinical chemistries and radiographic findings in these disorders.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

REFERENCES

Allen, R. H. et al., U.S. Pat. No. 4,940,568 (1990)
Allen, R. H. et al., U.S. Pat. No. 5,374,560 (1994)
Allen, R. H. et al., U.S. Pat. No. 5,438,017 (1995)
Allison, R. D., Methods in Enzymology, 113:419–437 (1985)
Amann, S. T. et al., Pancreas, 13:226:230 (1996)
Ammon, H. P. T. et al., Advances in Drug Research, 27:1–228 (1996)
Barrett, P. H. R. et al., Metabolism, 47:484–492 (1998)
Barshop, B. A. et al., Pediatric Research, 30:15–22 (1991)
Beaumier, L. et al., Biomed. Environ. Sci., 9:296–315 (1996)
Beckman, J. S. and Koppenol, W. H., Am. J. of Physiol., 271:C1424–C1437 (1996)
Benathan, M., British Journal of Dermatology, 137:721–727 (1997)
Bellini, M. et al., Alcohol and Alcoholism, 32:259–266 (1997)
Bianchi, G. et al., Journal of Hepatology, 26:606–613 (1997)
Bier, D. M., European Journal of Pediatrics, 156 (Supplement):S2–S8 (1997)
Bircher, J. and Preisig, R., Methods in Enzymology, 77:1–9 (1981)
Bostom, R. et al., Clinical Chemistry, 41:948–949 (1995)
Bourne, D. W. A. *Mathematical Modeling of Pharmacokinetic Data,* Lancaster (Pa): Technomic Publishing Company, 1–139 (1995)
Bressler, P. et al., Diabetologia, 39:1345–1350 (1996)
Browne, T. R. et al., Journal of Clinical Pharmacology, 33:246–252 (1993)
Browne, T. R. (Ed.), *Stable Isotopes in Pharmaceutical Research,* Amsterdam: Elsevier, 1–219 (1997)
Castillo, L. et al., Pro. Nat'l Acad. Sci. (USA), 91:6393–6397 (1994)
Castillo, L. et al., Am. J. of Physiol., 268:E360–E367 (1995)
Castillo, L. et al., Proc. Nat'l Acad. Sci. (USA), 93:11460–11465 (1996)
Caughey, G. H., Am. J. Resp., Cell and Mol. Biol., 4:387–394 (1991)
Charton, M. Methods in Enzymology, 112:323–346 (1985)
Cobelli, C. et al., Am. J. of Physiol., 253:E551–E564 (1987)
Cobelli, C. et al., Am. J. of Physiol., 262:E968–E975 (1992)
Colombato, P. et al., Journal of Viral Hepatitis, 4:143 (1997)
Cook, H. T. and Cattell, V., Clinical Science, 91:375–384 (1996)
Crane, B. R. et al., Science, 278(5337):425–431 (1997)
D'Argenio, D. Z., (Ed.),*Adv. Meth. of Pharmacokinetic and Pharmacodynamic Systems Analysis,* New York: Plenum Press, 3–211 (1991)

Davidson, W. D., Metabolism, 30:596–611 (1981)
Deshmukh, D. R. et al., Archives of Physiol. and Biochem., 105:32–37 (1997)
Douglas, K. T., in Dolphin, D. et al., (Eds.), Glutathione, New York: Wiley, 243–279 (1989)
El-Khoury, A. E., Am. J. of Physiol., 271:E563–E573 (1996)
Ferrari, R. et al., Am. J. of Med., 91(Supplement 3C):95S–105S (1991)
Fonseca, V. A. et al., Metabolism, 47:686–689 (1998)
Giorgi, G. et al., Current Therapeutic Research, 52:461–467 (1992)
Goldberg D. M. and Durie, P., Clinical Biochemistry, 26:253–275 (1993)
Griffith, O. W., Methods in Enzymology, 113:461–468 (1985)
Guttormsen A. B. et al., Am. Journal of Clinical Nutrition, 63:194–202 (1996)
Hansch, C., Drug Metabolism Reviews, 1:1–14 (1972)
Hasegawa, T. et al., Journal of Pediatric Surgery, 32:1548–1551 (1997)
Hebert, L.F. et al., Journal of Clinical Investigation, 98:930–936 (1996)
Hecker, M. et al., FEBS Letters, 294:221–224 (1991)
Heinzel, G. et al., *TopFit* (Version 2), Stuttgart: Gustav Fischer, 1.5–5.133 (1993)
Hellerstein, S. L., U.S. Pat. No. 5,338,686 (1994)
Herzenberg L. A. et al., Proc. Nat'l Acad. Sci. (USA), 94:1967–72 (1997)
Hofman, A. S. and Cole, S. G., U.S. Pat. No. 4,676,974 (1987)
Holgate, S. T., Ciba Foundation Symposium, 206:5–34 (1997)
Hull, J. et al., Thorax, 52:557–560 (1997)
Imondi, R. A., U.S. Patent No. 3,806,592 (19174)
Jackson, A. A. et al., Journal of Nutrition, 126:2814–2822 (1996)
Kalayjian, R. C. et al., Journal of Acquired Immune Deficiency Syndromes, 7:369–374 (1994)
Katz, J. Metabolism, 38:728–733 1989)
Klein, E. R. and Klein, P. D. (Eds.), *Stable Isotopes, Proc. Third International Conf.*, New York: Academic Press, 1–304 (1979)
Klein, P. D. et al., U.S. Pat. No. 5,233,997 (1993)
Kolhouse, J. F. et al., U.S. Pat. No. 5,506,147 (1996)
Kyle, D. J., U.S. Pat. No. 5,466,434 (1995)
Lagerwerf, F. M. et al., Analytical Biochemistry, 257:45–52 (1998)
Laghi, V. et al., Hepato-Gastroenterology, 44:1182–1186 (1997)
Lange, G. L. et al., U.S. Pat. No. 5,432,058 (1995)
Lassen, N. A. and Perl, W. *Tracer Kinetic Methods in Medical Physiology*, New York: Raven Press, 1–189 (1979)
Levy, M. A. et al., Journal of Nutrition, 128:671–676 (1998)
Liao, Y. and Husain, A., Canad. J. of Cardiol., 11(Suppl. F):13F–19F (1995)
Malloy, C. R. et al., U.S. Pat. No. 5,413,917 (1995)
Marschall, H. -U. et al., J. of Biol. Chem., 264:12989–12993 (1989)
Maury, C. P. J. Clinical Chemistry, 27:2058–2060 (1981)
McClain, D. and Crook, E. D. Diabetes, 45:1003–1009 (1996)
McCully, K. S. Annals of Clinical and Laboratory Science, 24:134–152 (1994)
McKnight, G. L. et al., W.O. Patent No. 93/21330 (1993)
Meister, A., Methods in Enzymology, 113:438–445 (1985)
Meister, A., in Dolphin, D. et al., (Eds.), *Glutathione*, New York: Wiley, 367–474 (1989)
Meister, A. and Griffith, O. W., Methods in Enzymology, 113:445–451 (1985)
Mohan, O. E. et al., Respiration Physiology 86:159–170 (1991)
Nerlich, A. G. et al., Diabetes, 47:170–178 (1998)
Nilsson, K. et al., Europ. J. of Clin. Invest., 26:853–859 (1996)
Nishi, K. et al. European Patent No. 0 824 149 A2 (1998)
Nissen, S. L., et al., U.S. Pat. No. 5,628,328 (1997)
Nygard, O. et al., N. E. J. of Med. 337:230–236 (1997)
Oberley, L. W., Free Radical Biology and Medicine, 5:113–124 (1998)
Ohlhauser, C. et al., Onkologie, 20:126–131 (1997)
Packer, L. (Ed.), *Nitric Oxide (Part A, Methods in Enzymology, Vol.* 268), 1–489 (1996)
Packer, L. (Ed.), *Nitric Oxide (Part B, Methods in Enzymology, Vol.* 269), 1–467 (1996)
Patterson, B., Metabolism, 46:322–329 (1997)
Pawlotsky, J. M. et al., Journal of Medical Virology, 54:26–37 (1998)
Picot, D. et al., Gastroenterol. Clinique et Biologique, 21:562–566 (1997)
Redgrave, T. G. and Martins, I. J., U.S. Pat. No. 5,756,067 (1998)
Rinderknecht, H. in Go, V. L. W. et al., (Eds.), *The Exocrine Pancreas: Biology, Pathophysiology, and Diseases,* New York: Raven Press, 163–183 (1986)
Robinson, G. B., Biochemical Journal, 108:275–285 (1968)
Shankar, R. R. et al., Metabolism, 47:573–577 (1998)
Sies, H. (Ed.), *Antioxidants in Disease Mechanisms and Therapy (Advances in Pharmacology, Vol.* 38), 1–415 (1997)
Simonian, N. A. and Coyle, J. T., Ann. Rev. Pharmacol. and Toxicol. 36:83–106 (1996)
Stamler, J. S. and Slikva, A., Nutrition Reviews, 1:1–130 (1996)
Szewczuk, A. and Wellman-Bednawska, M., Clinica Chimica Acta, 84:19–26 (1978)
Tate, S. S. and Meister, A., Methods in Enzymology, 113:400–419 (1985)
Topliss, J. G., (Ed.), *Quantitative Structure-Activity Relationships of Drugs,* New York: Academic Press, 1–375 (1983)
Tsai, K. et al., Gut, 42:850–855 (1988)
Vann, L. S. et al., Proceedings of the Western Pharmacology Society 20:91–95 (1977)
Vita, J. A. et al., Journal of Clinical Investigation 101:1408–1414 (1998)
Wagner, D. A. et al., U.S. Pat. No. 5,386,832 (1995)
Wagner, J. G., J. Pharmacokinetics and Biopharmaceutics, 5:443–478 (1976)
Wagner, J. G. *Pharmacokinetics for the Pharmaceutical Scientist,* Lancaster (Pa): Technomics Publishing Co., 1–316 (1993)
Watkins, P. B., U.S. Pat. No. 5,100,779 (1992)
Weichert, W. and de Graaf, A. A., Advances in Biochemical Engineering, 54:1–151 (1996)
White, R. D. et al., Acute Toxicity Data, 1:164–165 (1992)
Wolfe, R. R., Radioactive and Stable Isotope Tracers in Medicine, New York: Wiley-Liss, 1–395 (1992)
Yokoi, I. Et al., Neuropharmacology, 33:1261–1265 (1994)

What is claimed is:

1. A method of determining the in vivo conversion activity in mammals of a Class I, II or III gateway enzyme, said method comprising the steps of:

identifying a Class I, II or III gateway enzyme to be assayed;

designing a labelled metaprobe to have substrate specificity for said enzyme, said metaprobe further being designed so that when acred upon by said enzyme in vivo, at least one labelled end product that s directly detectable is produced;

administering to a mammalian subject a defined trace amount of said labelled metaprobe; and determining the extent of in- vivo conversion of said metaprobe to said labelled end product by said enzyme.

2. The method of claim 1 wherein said gateway enzyme is a Class I gateway enzyme selected from the group consisting of arginase, chymotrypsin, cytaticnine sythase, γ-glutamyl transpeptidase, glutathione-S-transferase, palmitoyl transferase, phosnholipase-A2 and pancreatic trypsin.

3. The method of claim 1 wherein said gateway enzyme is a Class II gateway enzyme selected from the group consisting of alanine-glyoxylate aminotransferase, elastase, glutamine-fructose-6-phosphate aminotransferase, α-ketoacid decarboxylase (mitochondrial), liver N-acetyl transferase (Nat1), microsomal oxidase (P450 dependent), oxoprolinase and sulfite oxidase.

4. The method of claim 1 wherein said gateway enzyme is a Class III gateway enzyme selected from the group consisting of angiotensin converting enzyme, human HIV protease, nitric oxide synthase and peroxysomal peroxidase.

5. The method of claim 1 wherein said metaprobe comprises a labelled release tag which is cleaved from said tracer probe upon gateway enzymatic action.

6. The method of claim 1 wherein said release tag is enzymatically converted to produce a metabolic end product of said organism.

7. The method of claim 1 wherein said label comprises a stable isotope.

8. The method of claim 1 wherein, in said administering step, said labelled metaprobe is directed to a specific pool of said enzyme in said patient.

9. The method of claim 1 wherein said patient is a human patient.

10. The method of claim 1 wherein said patient is a non-human mammal.

11. The method of claim 1 wherein said determining step is carried out upon expired breath from said patient.

12. The method of claim 1 wherein said determining step is carried out upon a plasma sample from said patient.

13. The method of claim 1 wherein said gateway enzyme is oxoprolinase, said metaprobe is $^{13}C$-L-2-oxothiazolidine-4-carboxylic acid and said labelled end product is $^{13}CO_2$.

14. The method of claim 1 wherein said gateway enzyme is chymotrypsin and said metaprobe is N-acetyl-L-phenylalanyl-L-leucyl[1-$^{13}C$]-(4'-carbethoxy)-acetanilide.

15. The method of claim 1 wherein said gateway enzyme is chymotrypsin and said metaprobe is N-acetyl-L-phenylalanyl-L- 2-aminobutyryl[1-$^{13}C$]-(4'-carbethoxy)-acetanilide.

16. The method of claim 1 wherein said gateway enzyme is cystathionine synthase and said metaprobe is L-2-oxo-tetrahydro-1,3-thiazine-4-carboxylic acid ethyl ester.

17. The method of claim 1 wherein said gateway enzyme is glutamine-fructose-6-phosphate aminotransferase and said metaprobe is L-N-acetyl-glutamine[2-$^{15}N$].

18. The method of claim 1 wherein said gateway enzyme is γ-glutamyl transpeptidase and said metaprobe is L-1-carbethoxy-2-acetamido-5-glutamyl-L-2-aminobutyryl[1-$^3C$]-glycine.

19. The method of claim 1 wherein said gateway enzyme is γ-glutamyl transpeptidase and said metaprobe is L-1-carbethoxy-2-acetamido-5-glutamyl-L-2-aminobutyryl[1-$^{13}C$]-(4'-carbethoxy)-acetanilide.

20. The method of claim 1 wherein said gateway enzyme is γ-glutamyl transpeptidase and said metaprobe is L-1-carbethoxy-[1-$^{13}C$]-2-acetamido-5-glutamyl-(4'-carbethoxy)-acetanilide.

21. The method of claim 1 wherein said gateway enzyme is α-ketoacid decarboxylase and said metaprobe is L-N-acetyl-2-aminobutyric[1-$^{13}C$] acid.

22. The method of claim 1 wherein said gateway enzyme is liver N-acetyl transferase and said metaprobe is L-N-acetyl-2-glucosamine[1-$^{13}C$].

23. The method of claim 1 wherein said gateway enzyme is nitric oxide synthase and said metaprobe is L-homo-arginine[guanidino-$^{15}N_2$].

24. The method of claim 1 wherein said gateway enzyme is nitric oxide synthase and said metaprobe is 5-guanidino [$^{15}N_2$] valeric acid.

25. A method of determining a medical condition in a patient, said method comprising the steps of:

identifying a Class I, II or III gateway enzyme from a biochemical pathway related to said medical condition;

selecting a labelled metaprobe for said enzyme, said metaprobe being selected so that when acted upon by said enzyme, at least one labelled end product that is directly detectable is produced;

administering to said patient a defined amount of said labelled metaprobe;

determining the extent of conversion of said metaprobe to said labelled end product by said enzyme in said patient; and using the extent of conversion of said metaprobe to said product to determine said medical condition.

26. A method of monitoring the status of a medical condition in a patient, said method comprising the steps of:

identifying a Class I, II or III gateway enzyme from a biochemical pathway related to said medical condition;

selecting a labelled metaprobe for said enzyme, said metaprobe being selected so that when acted upon by said enzyme, at least one labelled end product that is directly detectable is produced;

determining in a patient a metabolic index value for said gateway enzyme by carrying out steps comprising:
administering to said patient a defined amount of said labelled metaprobe,
determining the extent of conversion of said metaprobe to said labelled end product by said enzyme in said patient, and
using the extent of conversion of said metaprobe to said product to determine said metabolic index value for said enzyme in said patient;

obtaining a normative metabolic index value for said gateway enzyme determined in one or more individuals selected from a clinical population by carrying out steps comprising:
administering to said one or more selected individuals a defined amount of said labelled metaprobe, determining the extent of conversion of said metaprobe to said labelled end product by said enzyme in said one or more selected individuals, and using the extent of conversion of said metaprobe to said product to determine said metabolic index value for said enzyme in said one or more selected individuals; and comparing said metabolic index value for said enzyme in said patient with said metabolic index value for said enzyme in said one or more selected individuals.

27. A method of managing a medical condition in a patient comprising carrying out the method of claim 25, and selecting a therapeutic intervention appropriate for said medical condition.

28. The method of claim 27 wherein said therapeutic intervention comprises initiating a therapeutic pharmaceutical treatment.

29. The method of claim 27 wherein said therapeutic intervention comprises adjusting a therapeutic pharmaceutical treatment.

30. The method of claim 27 wherein said therapeutic intervention comprises initiating a nutritional support regimen.

31. The method of claim 27 wherein said therapeutic intervention comprises adjusting a nutritional support regimen.

* * * * *